United States Patent
Chung et al.

(10) Patent No.: US 10,055,549 B2
(45) Date of Patent: Aug. 21, 2018

(54) METHOD AND APPARATUS FOR WIRELESS HEALTH MONITORING AND EMERGENT CONDITION PREDICTION

(71) Applicant: Wireless Medical Monitoring, Inc., San Francisco, CA (US)

(72) Inventors: Wayne Chung, San Francisco, CA (US); Anthony Kaveh, Hillsborough, CA (US)

(73) Assignee: Wireless Medical Monitoring, Inc., San Francisco, CA (US)

( * ) Notice: Subject to any disclaimer, the term of this patent is extended or adjusted under 35 U.S.C. 154(b) by 145 days.

(21) Appl. No.: 14/050,356

(22) Filed: Oct. 10, 2013

(65) Prior Publication Data

US 2015/0106020 A1    Apr. 16, 2015

(51) Int. Cl.
| | | |
|---|---|---|
| *A61B 7/00* | (2006.01) | |
| *G06F 19/00* | (2018.01) | |
| *G16H 50/30* | (2018.01) | |
| *G16H 50/20* | (2018.01) | |

(52) U.S. Cl.
CPC ........ *G06F 19/3418* (2013.01); *G06F 19/345* (2013.01); *G06F 19/3431* (2013.01); *G16H 50/20* (2018.01); *G16H 50/30* (2018.01)

(58) Field of Classification Search
CPC .............. A61B 7/003; A61B 7/04; A61B 7/00
USPC ....................................................... 600/586
See application file for complete search history.

(56) References Cited

U.S. PATENT DOCUMENTS

| | | | |
|---|---|---|---|
| 7,472,577 B2 * | 1/2009 | Shibuichi ................. | A61B 7/00 73/9 |
| 8,140,154 B2 * | 3/2012 | Donnelly et al. ................. | 607/6 |
| 2004/0068204 A1 * | 4/2004 | Imran .................. | A61B 5/0538 600/593 |
| 2005/0240087 A1 * | 10/2005 | Keenan et al. ............... | 600/301 |
| 2009/0054737 A1 * | 2/2009 | Magar .................. | A61B 5/0205 600/300 |
| 2009/0076345 A1 * | 3/2009 | Manicka .............. | A61B 5/4875 600/301 |
| 2009/0264792 A1 * | 10/2009 | Mazar .................. | A61B 5/0531 600/547 |
| 2009/0275848 A1 * | 11/2009 | Brockway et al. ........... | 600/513 |
| 2010/0120585 A1 * | 5/2010 | Quy .................................. | 482/8 |
| 2010/0217345 A1 * | 8/2010 | Wolfe .................... | A61B 5/024 607/17 |
| 2010/0234716 A1 * | 9/2010 | Engel .................. | A61B 5/02055 600/391 |
| 2011/0245711 A1 * | 10/2011 | Katra et al. .................... | 600/547 |
| 2011/0319954 A1 * | 12/2011 | Niazi ..................... | A61B 5/686 607/17 |
| 2012/0220835 A1 * | 8/2012 | Chung .......................... | 600/301 |

(Continued)

*Primary Examiner* — Daniel Cerioni
(74) *Attorney, Agent, or Firm* — Amin, Turocy & Watson, LLP

(57) ABSTRACT

The present invention relates generally to an adherent sensor patch for wireless and remote physiological monitoring and evaluation of health and disease state of a patient wearing the patch, and specifically with respect to cardiac and pulmonary pathologies, including heart failure and sleep apnea. Data generated by the patch, which includes a microphone sensor and other sensors, is processed by a remote server and is made accessible to caregivers and also used to manage, calibrate and control the operations of the sensors of the patch.

13 Claims, 13 Drawing Sheets

(56) References Cited

U.S. PATENT DOCUMENTS

| | | | |
|---|---|---|---|
| 2014/0081092 A1* | 3/2014 | McNair | A61B 5/021 600/301 |
| 2015/0164340 A1* | 6/2015 | Bedingham | A61B 7/04 600/484 |
| 2015/0250445 A1* | 9/2015 | Spiegel | A61B 7/008 600/301 |

* cited by examiner

METHOD AND APPARATUS FOR WIRELESS HEALTH MONITORING AND EMERGENT CONDITION PREDICTION

BACKGROUND OF THE INVENTION

Cardiovascular disease is the leading cause of death in the United States with many deaths attributable to preventive causes. Congestive heart failure (CHF), as an emerging epidemic with significant burden on hospitalizations, quality of life, and societal cost, warrants special attention. It has experienced little improvement in hospital admissions in the past three decades and is a leading cause of death in the United States with approximately 670,000 individuals diagnosed every year. It is also an end-stage condition reached by many with other cardiovascular diseases, such as diabetes, hypertension, and atherosclerosis, all of which are increasing in prevalence at alarming rates in the United States.

The clinical course of CHF has also been well documented. Given the known inciting events preceding hospitalization, the lack of methods to accurately predict these changes, and frequency of decompensation resulting in recurrent hospitalizations, experts believe that constant monitoring of patients with CHF is essential to a patient's health.

Remote sensing has thus emerged as a twofold solution to the unsustainable trends in treating heart failure by also expanding healthcare access and clinical surveillance to the growing demographics that are at-risk, limited in healthcare access, or both. While various medical specialties have attempted to implement remote monitoring solutions with varying levels of success, at least some methods for longitudinal monitoring are limited or unreliable in detecting emergent conditions as reflected in significant rehospitalization rates and resultant economic burden, such as from ambulance costs and emergency room visits. At least some of these monitoring methods may suffer from a paucity of physiological sensed quantities, obtrusive sensing requirements, noise or artifact corruption, or poor classification algorithms.

In the field of cardiology, many sensors may report information with heavy dependence on a measure such as body weight, EKG, or transthoracic impedance with limited potential for evaluating more integrated phenomena, such as heart failure status. Though some recent efforts have shown potential for early prediction of emergent conditions by including addition sensors, these approaches have not yet fully applied analytical and statistical tools for an automated biocomputational approach to disease modeling and intervention with acceptable performance or clinical adoption, as in the remote monitoring of acute decompensated heart failure (ADHF). Heart failure is especially suited to remote monitoring because of its inordinate toll on society, the indolent progression of disease, and the ineffective treatment methods currently available for those suffering recent myocardial infarction or other cardiac insult.

For effective longitudinal monitoring, the classification and disease progression computation must maximize acquisition of ideal data points, hence requiring patient compliance over a long time course, such as six or twelve months. Inconvenient or uncomfortable device placement or weight, limitations on physical activity, prohibitive costs, and supervised data transmission or general use are examples of barriers to long term patient compliance. Preferred embodiments of the present invention allow for continuous or substantially continuous monitoring with an external and cost-efficient adherent patch. The patch may use existing cellular infrastructure to disseminate processing and decrease computation load in confined spaces to realize power and memory savings and provide a more comfortable device with smaller battery and memory requirements, allowing for a more economical sensor able to benefit more individuals with remote monitoring to track health or disease status and predict emergent conditions, such as ADHF.

The presented invention addresses this need for improved remote monitoring of physiological measures implicated in chronic pathologies by using a classification algorithm to monitor individuals and alert caregivers to health and disease state and probability of future emergent conditions. This method is enabled by disseminated processing to allow for comprehensive health modeling, improved patient compliance, and economic feasibility of the multisensor device. While an embodiment of this invention can be applied to monitoring general health or chronic pathologies such as heart failure, many other conditions can be monitored, including but in no way limited to, diabetes, obesity, depression, epilepsy, respiratory diseases, or hypertension, independent of etiology.

SUMMARY OF THE INVENTION

The present invention relates a method and apparatus to the remote monitoring of ambulatory patients suffering from a range of pathologies that involve, either directly or indirectly, the function of the cardiac and pulmonary systems. A plurality of physiologically independent sensors integrated into an adherent patch comprise a patient monitoring device that records data and variably processes data along a transmission route ultimately to a remote server. The objective is to monitor the progression of a particular pathology, classify the stage of disease, and predict imminent decompensation with sufficient time lead as to offer potentially life-saving intervention and reduce hospital readmissions. Outputs from the stages of processing and classification are made available to healthcare providers or others involved in the care of the patient in various forms, including but not limited to, electronic summary reports or alerts.

Sensed physiological quantities can include, by way of example and in no way limiting, respiratory effort, temperature, thoracic impedance, electrocardiogram (EKG), heart sounds (S1, S2, S3, S4), lung sounds (crackles, rales), patient activity, and numerous linear and non-linear fusions and combinations of any sensed quantities.

By virtue of coincident and simultaneous sensing, these quantities may be processed, by way of example and in no way limiting, with filters, fusions, cross-sensor validation, trend removal, compression, or averaging at any stage in a data transmission route comprising patient monitoring device, intermediate device such as a smartphone, and remote server. The aim of the data transmission scheme is to maximize data acquisition and enable disseminated processing to reduce computational load in confined spaces. This allows for increased device comfort and minimized disruption to patient lifestyle to enhance longitudinal monitoring of chronic disease. For example, by using a GPS enabled smartphone as an intermediate device, information regarding geographic location, distance from nearest healthcare provider, movement, social communication, questionnaires from the physician or researchers, and many other parameters can be obtained without excess hardware burden on the adherent patch.

The objective of sensing, processing, and deriving physiological, social, and clinical quantities is to construct attributes specialized to the hardware design of the sensing device to guide health state classification. These attributes may be derived by a variety of methods described in the application and mathematically transformed to features in a different space, such as one in higher dimensions. The feature vector is input to a classifier to monitor the state of health or disease of the sensed individual and provide a composite index on their status for simplified interpretation of the large data set. The choice of classifier and input features may be evaluated to optimize performance by using methods described in the application. The composite index value may be followed over time for simplified longitudinal monitoring of an individual. Such a method allows for monitoring of healthy individuals, such as training athletes, or of ill patients, such as those suffering from acute or chronic conditions including heart failure or sleep apnea. By encrypting transmitted and stored data at a remote server, data can be securely accessed by all members involved in an individual's care with appropriate authentication and levels of data detail or interfaces.

Such a classification scheme can output information at various levels of detail depending on the end-user application. A high level output may involve a binary indicator to inform of healthy or emergent condition at the present time. This is known to be useful for efficient workflow, such as in heart failure remote monitoring for acute decompensation.

A deeper level of data detail includes health or disease progression from an arbitrary past point in time. An ideal past time point is a baseline determined in the presence of a health professional whose clinical judgment at the time of discharge may also be an attribute used in the classification system.

A further level of detail includes the probability of the individual developing an emergent condition in the future. This can prompt intervention in many forms, including, but not limited to, intervention by device, change in medication dosage, such as an oral diuretic treatment, or physical or electronic medical or surgical intervention. Examples of device intervention include defibrillation, drug infusion, and pacing.

A further level of detail shows temporal information about an individual's condition over an arbitrary time scale to monitor physiological dynamics. Such events include circadian rhythm, such as temperature changes from the effects of circadian hormone pulsations and medication usage. Examples of medications that may change physiological parameters, such as impedance or arrhythmia occurrence, include insulin, ACE inhibitors, beta adrenergic blockers, and diuretics. Temporal events, such as medication administration, can also be determined based on user interaction with the smartphone and correlated with physiological measures.

While a preferred embodiment of these methods applies to remote, ambulatory monitoring, such as in an outpatient setting, these methods can also be applied to sensing individuals in hospitals or in the intraoperative setting.

Embodiments of the present invention address the existing limitations in remote sensing with an external multisensor adherent patch device that leverages disseminated processing to increase the predictive power of specialized hardware sensors in modeling, classifying, and predicting health state while improving patient compliance. Various embodiments may also be used in research settings for the acquisition and processing of biological signals, such as for population scale computational modeling of cardiac, respiratory, autonomic, or system-wide phenomena. Such solutions may increase diagnostic accuracy and patient compliance while reducing costs and intervention time to facilitate improved chronic disease care.

DETAILED DESCRIPTION OF THE INVENTION

Embodiments of the present invention offer a method, system, and device for non-invasive physiological sensing for monitoring of health or disease state and prediction of emergent conditions, such as to allow for intervention or other preventive measures to be taken.

Figure 1:
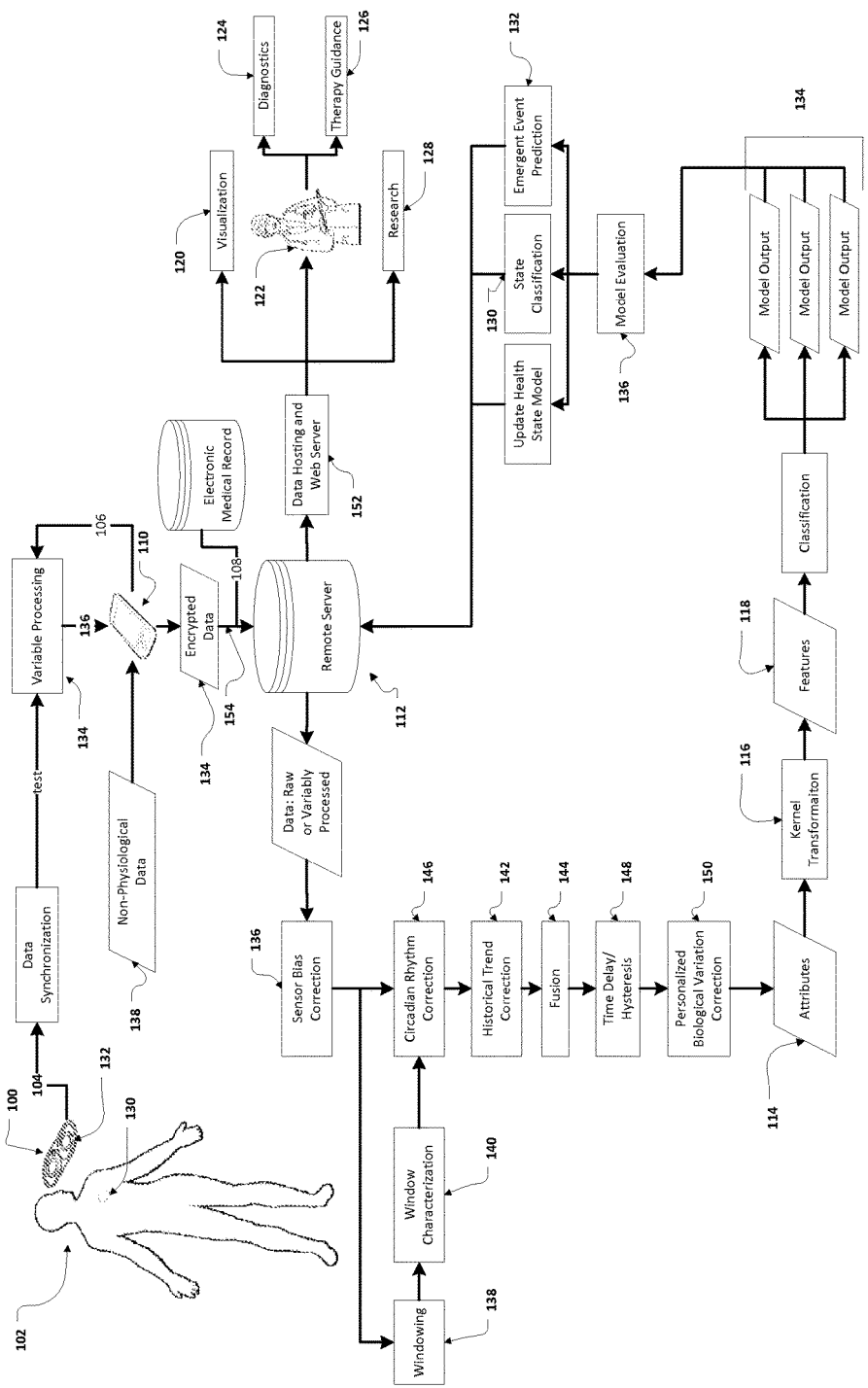
FIG. 1 shows an embodiment of data acquisition and processing from the sensing device through intermediate device through remote server for interaction with healthcare team.

An important aspect of the present invention is the simultaneous and coincident recording by a plurality of sensors for use in fusion and correlation of physiologically distinct phenomena, FIG. 1. This allows for enhanced characterization of a patient's state of health and may reveal subtle changes in physiology or systems physiology in response to everyday activity that may not be apparent from independently sensed quantities. This is accomplished by specializing algorithms to the characteristics and biases of the recording device 100, such as a multisensor adherent patch, adhered to a patient 102 to construct attributes 114 from raw, fused, corrected, or otherwise processed sensor outputs 104 that may be mathematically mapped 116 to a different space to form features 118. The feature vector may include rich physiological 104, social 138, and clinical 108 information to monitor health or disease progression, classify a particular state of health or disease, or predict the probability of an emergent condition.

The computation of data may be securely disseminated throughout stages of the system, such as on the adherent patch 100, on the intermediate device 110, or on the remote server 112, with appropriate encryption of patient health information (PHI). Results from this process may be securely hosted 152 on the remote server for a variety of reasons, such as visualization 120 by physician 122, diagnostics 124, therapy guidance 126, or research purposes 128.

General Device

The presented method for monitoring and classifying health or disease may obtain data from many types of devices and scenarios, such as inpatient for intraoperative monitoring or outpatient for surveillance. A preferred implementation is an adherent patch on the front torso 130 to minimize patient discomfort in various daily activities, such as sitting, sleeping, or walking, while still enabling access to physiological measurements. The presented invention uses methods to improve monitoring efficiency to reduce sensor size and weight to decrease disruption to daily activity and improve patient compliance in long term monitoring for increased clinical utility. The adherent patch may comprise a plurality of sensors as described above to accurately and timely monitor the physiological processes correlated to the individual's health status. The patch may be fixed in location using the adhesive 132 offered by the conductive pads for simplicity and ease of application. To accomplish the necessary sensing, processing, and data transmission, the device may also comprise a processor or controller, volatile memory, non-volatile memory, system clock, and wireless communication radio. As in FIG. 1, data may be sensed and variably processed 134 and encrypted prior to transmission 136 or alerting from device to intermediate device 110, such as smartphone, over a wireless protocol 154, such as Bluetooth or Wi-Fi. The smartphone may further process the data, such as by compression, before sending data to a remote server 112.

The device and algorithm are specialized to disseminate processing to allow for minimal space and power requirements at the stage of the sensing device 100. One of the limitations to minimizing sensing device footprint is the distance needed over which to measure the desired quantities. Examples of physiological measurements requiring a distance over which to perform measurement include EKG and thoracic impedance. One method for performing such measurements in a minimal space is to share electrode pairs across different sensors. For example, the EKG and impedance electrodes may be shared by programming a schedule for measuring for each quantity.

A further example seeks to maximize distance between electrode contacts with minimal discomfort to the sensed individual. As in FIG. 13, this may be accomplished with a smaller, secondary adherent patch 1300 that is coordinated with the primary adherent patch 1302. Information may be transferred between the sensors by a wireless or wired medium. The distance between the two patches may be determined empirically, such as related to body habitus, to maximize the physiological information obtained without inducing discomfort in the sensed individual.

In a preferred embodiment, the device may contain a method for event recording to enable the patient to signal their health status to their caregiver, such as their physician. An event may be recorded 206 by a variety of methods on the adherent device 226 or smartphone 228, such as a button press, voice command, or vigorous shaking to signal an acceleration sensor. As in FIG. 2, the action of event recording 206 may trigger alerts to the smartphone for immediate data transmission and alerting of a caregiver 232.

In a preferred embodiment, the device is capable of detecting acute conditions that require immediate intervention 208. Examples of such conditions include lethal arrhythmias, asystole, myocardial infarction, apnea, or other acute conditions. As in FIG. 2, the detection of such an emergent state 208 may trigger alerts 204 to the smartphone 222 for immediate data transmission and alerting of the caregiver 232.

In a preferred embodiment, the device may be used continually for many months or longer to enable the longitudinal surveillance of chronic diseases. To improve ease of use and patient compliance, the device may be reusable with proper cleansing and disinfection after use. Power requirements may be addressed with a battery that may or may not be removable, depending on the data continuity requirements of the specific monitoring scenario.

The device may be placed on the front torso of the individual with variability in placement depending on individual body habits and may be empirically determined in an initialization period to identify optimum placement. The placement may be recorded by a variety or means, such as with an image, diagram, anatomic marking, or guide. Any such guide may be made easily accessible from the intermediate smartphone device for reference.

The time points of device removal and replacement, as may be necessary during battery charging, battery replacement, electrode pad changes, or bathing, may be recorded to compute a compliance factor for the patient 138, as decreased patient compliance may be manifested by longer times than necessary without active device recording.

Figure 2:
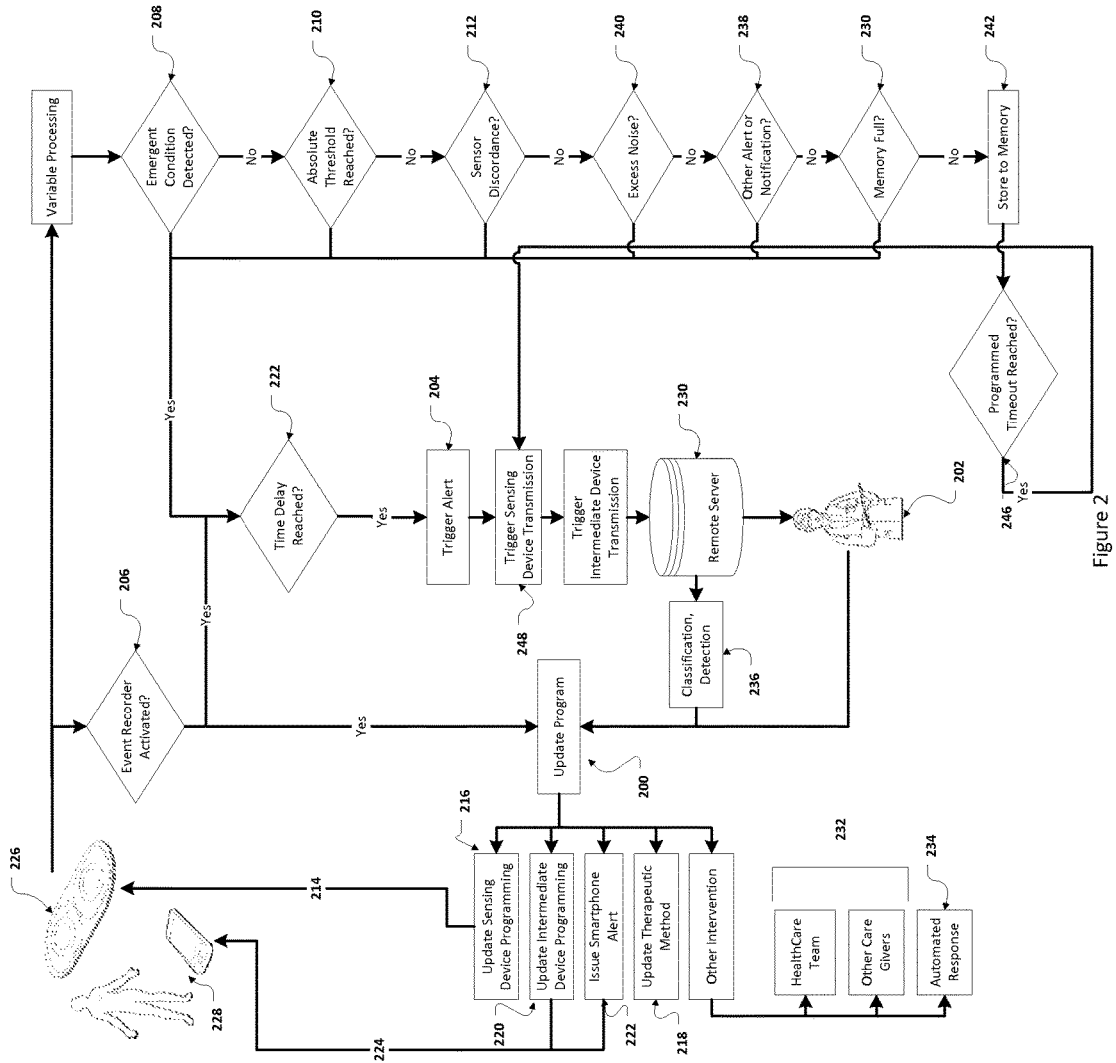
FIG. 2 shows the process of alert triggering for a variety of stimuli that may trigger an alert for healthcare provider or automated response.

The sensing device may be instantiated with default monitoring parameters that may be updated 200 over time for a variety of reasons, including learning from empiric historical data, clinical judgment 202, or alert statuses 204, such as from event recording activation 206, emergent conditions detected by the adherent device 208, crossing of absolute thresholds 210, or discordant sensor readings 212. FIG. 2 displays the programming method that may be initiated by the device itself or remotely 214 through the data transmission route described in this application, and may include functions 216 such as sensing parameters, data processing parameters, memory management, data transmission schedule, or alerting methods.

Embodiments of the device may include therapeutics for responding to detected health or disease states or classifications and may also be updated in response to such triggers 218. As an example, to prevent any discomfort or health risks associated with long term patch usage, the device may be coated with or otherwise release topical anti-microbial or anti-inflammatory treatments. A further example of drug treatments may be topical or injected, and may include cardiac related drugs to modify electrical activity. A further example of therapeutic intervention includes device-based therapy, such as alerts to devices providing temperature balance, pacing, defibrillation, or pump assist activity.

General Algorithm

As in FIG. 1, a remote server contains a database 112 that is updated by sensing devices. These data are used to monitor an individual's health and disease state by providing visualization of historical trending 120, classifying disease state 130, and predicting emergent conditions 132. The outputs from this algorithm may issue an alert or update to a healthcare provider 122, such as a physician or emergency medical services, depending on the health state and desired alerting level.

Encrypted data 134 received by the remote server may be raw or variably processed, depending on the data type and its use for detection of acute conditions necessitating expeditious processing. The received data may undergo a variety of operations in modules to prepare it as an attribute for health state classification. As an example, data may be pre-processed with methods including correction for sensor bias 136, windowing 138, window characterization 140, such as trend removal, averaging, or normalizing, correction for historical trends 142, or filtering, such as for electromagnetic interference.

As a further example, data may be fused across sensors to correct for coincident physiological or environmental conditions 144. As a further example, historical trend correction 142 may be augmented with learning algorithms to model the individual's biological variation with time or circadian rhythm 146. As a further example, historical values may be used to provide a time delay 148, such as a weighting that adjusts weights according to past similar values, to prevent spurious changes from triggering a false alert.

Figure 3:
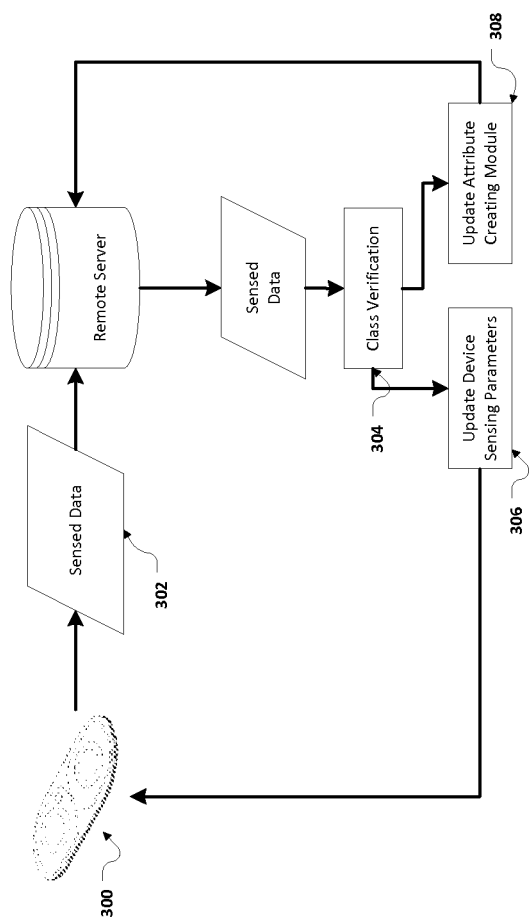
FIG. 3 presents a simplified outline of the method of training a monitoring algorithm with empiric sensor data.

As a further example, supervised and unsupervised learning algorithms may be applied to empiric historical data to learn personalized physiological information 150 about an individual and update sensing parameters, such as maximally responsive frequency ranges for acoustic or impedance signals, to better obtain physiological information and construct an attribute for classification. FIG. 3 presents a supervised learning method in which sensed data 302 from the adherent patch 300 measuring the state of health or physiology may be verified 304, such as by a physician or gold standard clinical measure, to update programming on the sensing device 306 and update downstream modeling and classification algorithms on the remote server 308.

Figure 4:
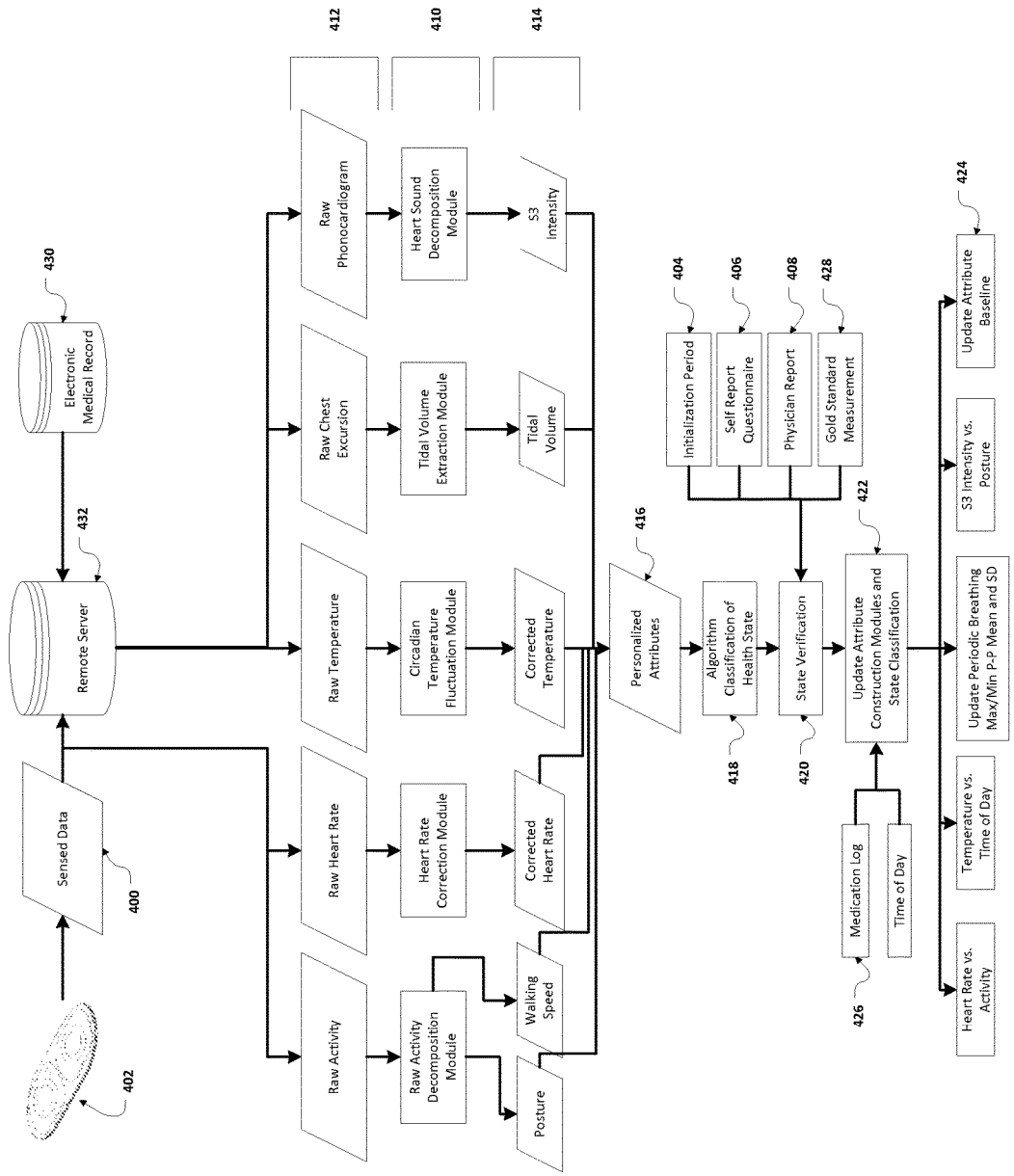
FIG. 4 shows a process of data acquisition, attribute construction, and feature transformation for classifying health or disease state. Methods for training the algorithm with verified data are presented appropriately.

FIG. 4 presents an embodiment in which such supervised learning is performed on sensed data 400 from the adherent patch 402 by individual learning modules trained with data obtained during an initialization period 404, by patient report 406, or obtained from a physician or other caregiver report 408. Individual modules 410 construct attributes from raw or variably processed sensor outputs 412 through methods including, but not limited to, filtering, fusion, mutual validation, and linear and non-linear corrections for sensor bias, biological variation, time of day, activity level, time delay, or historical trending. The resulting attributes 414 are hence personalized to account for the sensed individual's internal and external environment. The personalized attributes 416 may then be used to classify the sensed individual's health state and update their health modeling. The output of the health state classification algorithm 418 may then be verified 420 to further train 422 the classification algorithm 418 and the individual modules 410 involved in attribute construction.

Figure 5:
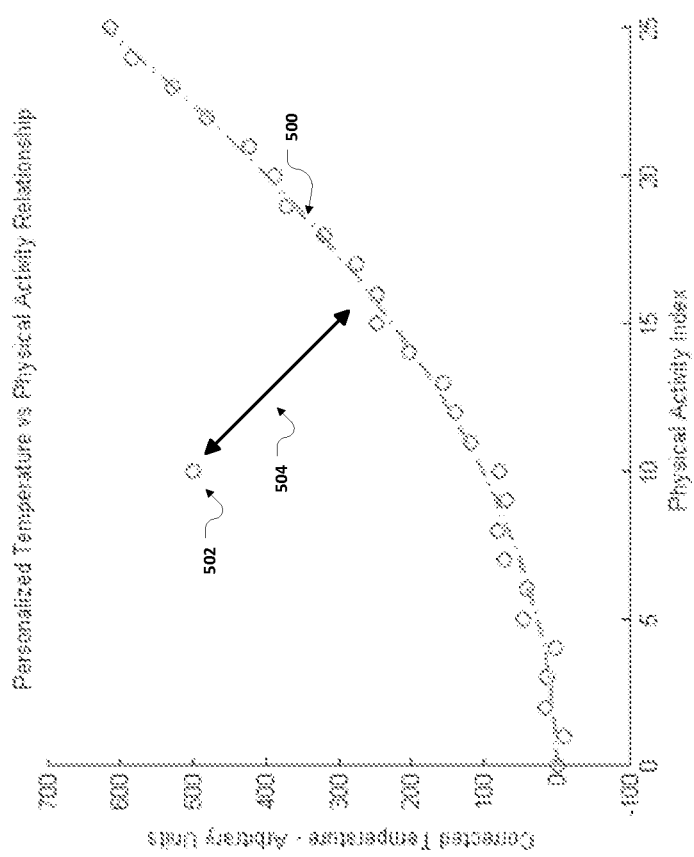
FIG. 5 shows a demonstrative graph of empiric sensor data that is used to construct a personalized physiological response curve.

Learning modules may be used to model biological variation and assign thresholds for an individual with training data. FIG. 5 represents measurements of a sensed individual's temperature response to physical activity. The pattern may be modeled 500, such as with a regression technique, to identify or weight data on distance from a distribution to determine a threshold crossing. For example, measurement 502 falls away from the sensed individual's historical distribution. The measurement may be characterized by a central tendency, such as a Euclidian distance 504, a measure of dispersion compared to existing empirical historic data, or a combination thereof. For example, a distance factor may be associated with the measurement as a ratio of distance and historical variation. The output may constitute an attribute having its own threshold, be transformed to an input feature to the general health state classifier, or both. Examples of learning models readily applied to this system include, but are in no way limited to, the perceptron algorithm and logistic or linear regression for modeling and neural networks and support vector machines for classification. Many optimization algorithms may be used for developing these algorithms, such as coordinate or gradient ascent or descent.

The continuous or dynamically sampled data may be windowed statically or dynamically over time for the aforementioned operations. Windowing may also be used to produce characteristic values over a time interval, including but not limited to, measures of central tendency, dispersion, time duration in a given state, rates of change, areas under the curve, spectral profiles, phase comparisons, maximum or minimal values in the time or frequency domain, or normalized values, such as percentages, z-scores, or other changes with respect to maximum or minimum, baseline, or other present or past values. Many of these operations may also be performed on singular points or groups of points if windowing over time is not performed. These operations may also be scaled across multiple windows to characterize extended time intervals, such as days, weeks, or months.

Figure 6:
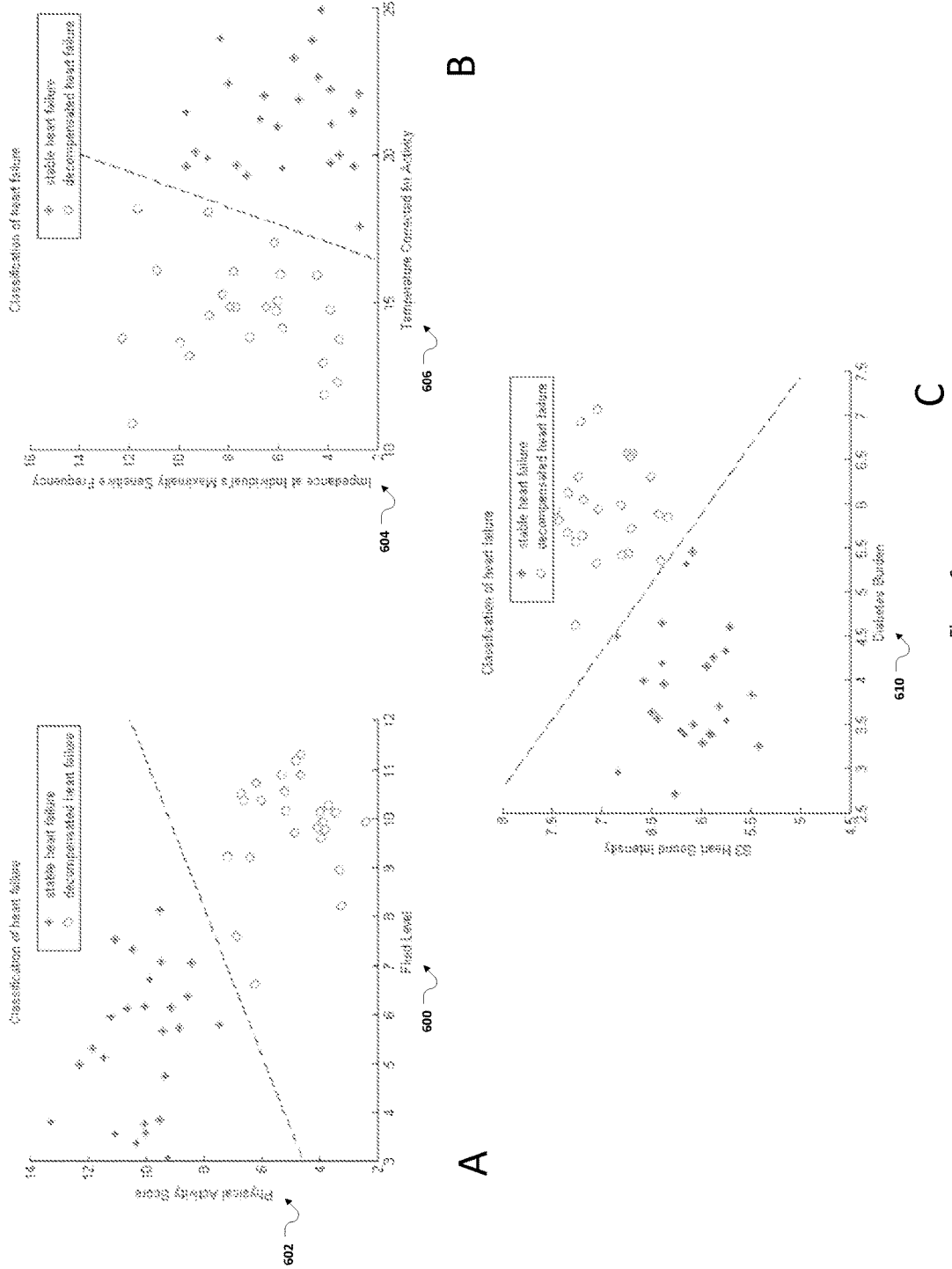
FIG. 6A-C shows demonstrative graphs of data used to classify disease state with a linear decision boundary based on derived attributes.

Once attributes are computed and combined 114, such as in vector form, they may be transformed 116 to a different space, such as one of higher dimensions. Such a transformation, such as with a kernel, will transform the attributes 114 to features 118. The feature vector will then be input into a classifier that will provide classification of disease state and measure of distance from a particular state. FIGS. 6a, 6b, and 6c represent 2 dimensional examples of a classification of heart failure based on features 600-610 derived from attributes themselves constructed by fused or otherwise processed data, such as 504 or 414. The preferred classification scheme may include a higher dimensional model space with more features.

As an algorithm is trained as in FIG. 1 with data from a sensing device 100 to learn appropriate decision boundaries for an input feature vector 118, it is desirable to identify the features that best describe the physiological system to avoid the undesirable effects of high dimensionality, such as over fitting. As such, different features may be used in different models 134 and evaluated 136 for performance using a comparison, such as cross-validation. Models of sufficient performance may also be evaluated and enhanced with stacked generalization. Different models 134 may also be formed with different classification algorithms, in addition to different features.

Figure 7:
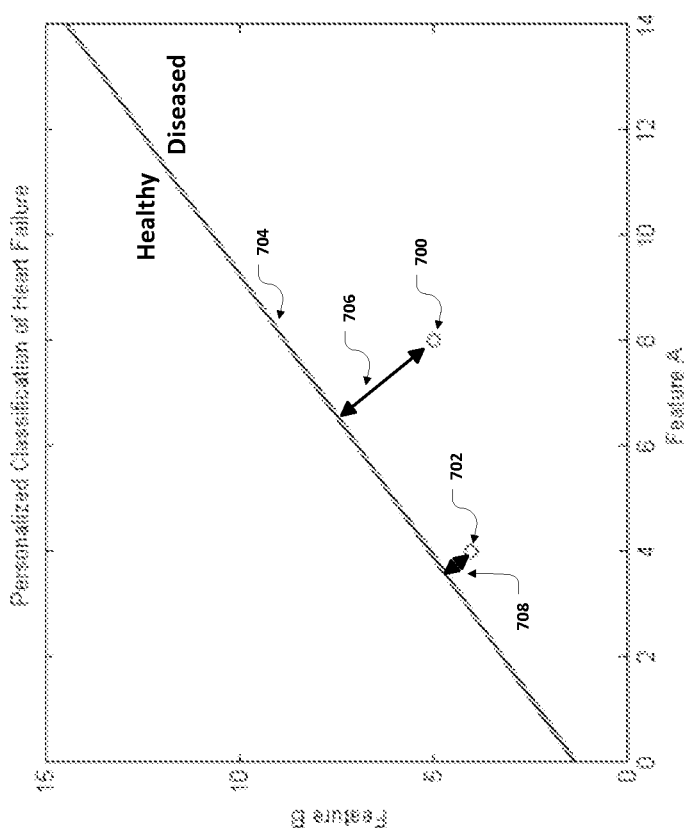
FIG. 7 shows a demonstrative graph of a linear decision boundary for healthy or diseased state and the distance of two data points from the boundary.
Figure 8:
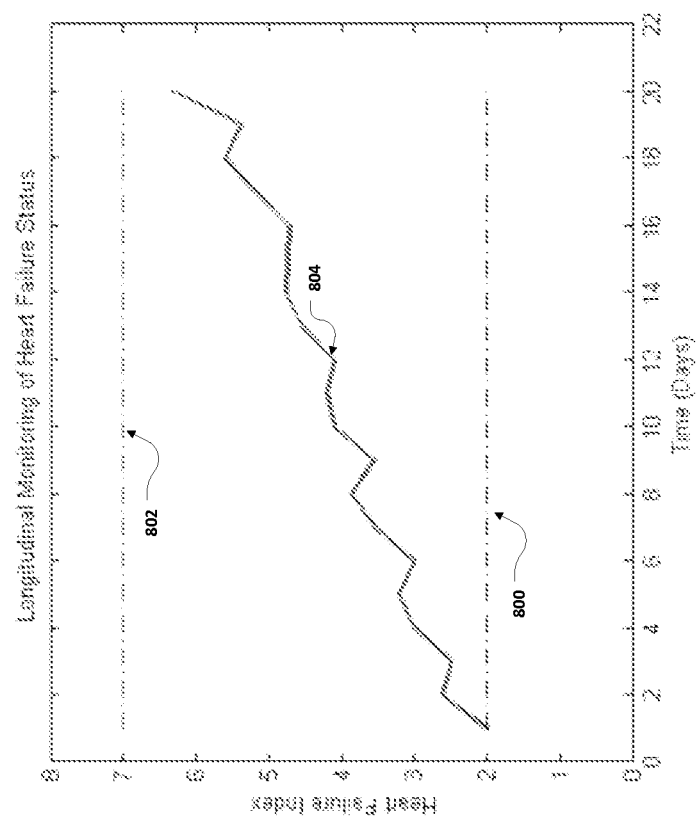
FIG. 8 shows a demonstrative graph of a derived health composite score plotted across time.

With a model or group of models identified, a decision boundary may be constructed by various classification methods to classify health state with respect to a particular pathology or groups of pathologies. For example, in classifying an emergent condition, such as acute decompensated heart failure (ADHF) in FIG. 7, the location of data points in a feature vector, such as 700 and 702, with respect to a decision boundary 704 can classify the state of the patient. Furthermore, the distance 706 or 708 of a feature vector 700 or 702 from a classification boundary 704 may be used to provide a composite value to summarize health status. A distance may be a Euclidian or weighted Euclidian distance, a Mahalanobis distance, or other distance or combination of distances. The composite score may then be stored and monitored in a visual format, as in FIG. 8, across time 804 for efficient evaluation of patient past and present health status. To aid in visualization, reference statistics may automatically be drawn, by way of example, for initial value 800 and alarm range 802. Similar visualizations may be presented for any of the individual attributes, such as 414, for ease of longitudinal monitoring of particular physiological or social attributes.

The monitoring and classification algorithm may run from the remote server and issue commands to each stage of the system, such as 214, 216, and 220. Examples of routines adjusted by the algorithm system at the device stage 216 include sensing and storing, modifying sampling rate on a per-sensor basis, performing immediate analysis for determination of acute disease states, setting data transmission schedules, and memory clearing.

Examples of intermediate device updating 220 by algorithm system include user notifications 222, user questionnaires or inquiries, interrogation of GPS status, adjustment of compression settings, or memory clearing.

System commands from the remote server to the sensing or intermediate devices may be initiated automatically or by a healthcare provider, such as to increase sampling in the setting of high clinical suspicion of an emergent condition.

Combinations

Figure 9:
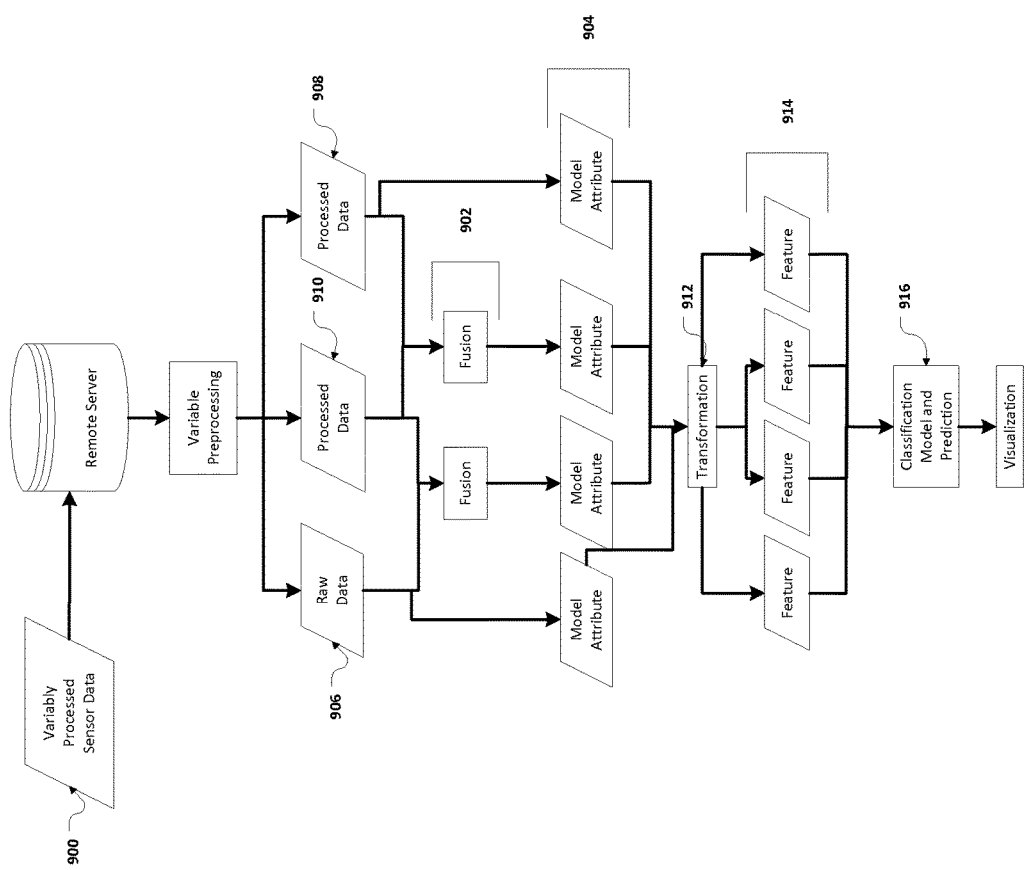
FIG. 9 shows the method of combining raw data and processed data through a fusion process for attribute construction.

As in FIG. 9, sensed quantities from individual sensors 900, such as EKG, impedance, accelerometer, temperature, or microphone, may be combined or fused 902 to derive independent physiological measures to construct classification attributes 904. Combinatory operations 902 may be performed on raw 906 or processed 908 or 910 values, with or without windowing. Examples of processed values include averages, detrended or filtered data, or data corrected for historical trends, personalized variation, and sensor bias. Examples of combinatory operations include, but are not limited to, logic gating, basic mathematical functions of weighted ratios of values, slopes, areas under the curve, or duration of time in given state, or spectral profiles to guide filtering. As described earlier, model attributes 904 may be transformed 912 to yield a feature vector 914 for modeling, classification, and prediction 916.

As an example, two processed attributes, such as body mass index (BMI) and thoracic impedance, may be fused to construct a new attribute that corrects for the fat content dependence of impedance as detailed in patent application US20110245711 that is hereby incorporated by reference in its entirety. This combination may allow for improved impedance measuring within the size, memory, and power restraints present in the sensing device. A further example is of EKG alternans and mechanical cardiac alternans, as detailed in patent application US20090275848 that is hereby incorporated by reference in its entirety, as detected by a chest-worn accelerometer to construct a new attribute to better characterize hemodynamic function. In the context of heart failure, weakened mechanical force of the heart may be manifest by reduced apical impulse and may mutually validate the electrical alternans sensed on the EKG for a more accurate quantification and prediction of heart failure. Mutual validation is a powerful tool in the context of high noise environments, such as those experienced by remote, ambulatory sensing with limited space, memory, and power.

Other examples of combinations may utilize derived quantities in part defined by presence or absence. For example, the EKG output can be further decomposed to reveal the presence or absence of a certain type of arrhythmia. The arrhythmia may also be quantified by number of occurrences per unit time, such as to construct an attribute of arrhythmia incidence index. Either result may then be combined with another parameter, such as heart rate, to construct a T-wave alternans (TWA) or heart rate turbulence (HRT) attribute. A further example is a discrete presence/absence attribute from clinical history, such as history of coronary artery disease. Once again, this binary value may be quantified by information such as years since diagnosis, disease severity, or percent of vessel occlusion to construct a coronary artery disease burden attribute, and either attribute may be used in fusion.

The additional attributes resulting from fusion may be combined with temporal profiles and magnitude effect sizes to distinguish mimicking disease states. Examples of disease states that may share symptomology include anatomical or infectious respiratory diseases, sleep apnea, various cardiac arrhythmias, renal failure, and heart failure from various causes. Such distinction is valuable in guiding the healthcare team to treat underlying pathological entities.

Threshold Updating

The present invention relates a method for monitoring health and disease that is personalized to patient-specific physiology and accordingly uses thresholds that account for patient characteristics, including medical history and past physiological trends in the form of attribute construction. As in FIG. 7, by using a model that innately includes these characteristics integrated with a continuous scale 704 for feature readings, the algorithm for assessing health and predicting emergent conditions avoids discrete thresholds that may be updated based on discrete boundary crossings of other sensors or attributes, as such methods may poorly account for biological variability, noise contamination, or insignificant fluctuations near a threshold. Instead of using a more simple yet limited discrete valued classification system, the present invention's attribute construction integrates correction factors, smartphone inputs, historical empiric data, and mutual sensor validation to produce features that are innately interdependent in classifying and predicting a condition.

Learning Modules

There is often much biological variability in the physiological quantities measured to assess health or disease. While this variability is often present between patients, much of the variation is consistent within a patient and can be corrected for by use of empiric data from past measurements. For example, a baseline heart rate across individuals may vary from 55-75 beats per minute, but will likely have a smaller variance within each individual, especially when corrected for activity level. To account for such variability in the sensed quantities 412, the preferred embodiment contains modules 410 to correct for these variations in constructing attributes for classification, as represented in FIG. 4. The personalization factors of sensed quantities to form attributes 414 can be learned during an initialization period 404 in which an individual or caregiver informs the sensing system 420 to the individual's current state. For example, the initialization period may present the individual in an equilibrium or normalcy state that is maintained for an extended period of time, such as 12 or 48 hours. If the sensed state is not in equilibrium, the correct classification may be made to train the modules 410 or classifier 418 accordingly 422. If individual attributes, such as within 414, are not in their normal state, they may also be classified appropriately.

A state of health can be characterized in many ways, including measures of central tendency and dispersion, maximum or minimum values, or normalized variations thereof, and may be taken across widows. In a preferred embodiment as in FIG. 5, a regression method may model the individual's biological response 500 in various environments, including resting states. 502 presents an excursion from the individual's learned response 500 and may be quantified by a variety of metrics, such as a Euclidian or weighted Euclidian distance, a Mahalanobis distance, or other characterization distance or combination thereof, from the healthy state curve. The distance measure 504 may then be used to construct an attribute that innately accounts for the individual's biological variation.

FIG. 4 represents an embodiment that uses the questionnaire ability of the smartphone 406 to directly ask the patient questions to ascertain patient state and use the response to personalize sensor data in the form of training attribute modules 410 with 420. An example of the utility of this method is in slow fluctuations of baseline measures that may occur after the initialization period or if an initialization period is unavailable. Such personalization or correction of thresholds may be derived from regression models or other online learning methods, such as the perceptron algorithm.

Another example of personalization is based on the sensed individual's circadian rhythm, in which it is well known that physiological quantities, such as baseline temperature, are dependent on the hour of day or fluctuate with respect to sleep/awake cycles independent of physical activity. The sensors used in the present method, such as the accelerometer, can readily determine sleep/awake cycles and hence enable such correction to minimize biological variation and improve consistency in assessing long term temperature equilibrium.

A similar example is of the correlation between activity or movement and temperature changes. Increased activity is known to cause an increase in temperature due to metabolic demand whose magnitude of change may or may not be pathological. The degree of change in temperature relative to change in activity level may be learned for a specific individual as data collection progresses, and significant variations from the adjusted, personalized values may be indicative of emergent conditions as detailed in U.S. Pat. No. 6,821,249 that is hereby incorporated by reference in its entirety. This correction thus serves to both assess temperature response to metabolic activity and correct temperature readings by activity level, which may be a significant noise source in long term ambulatory monitoring where daily activities are encouraged.

A further example utilizes the smartphone's capabilities in various forms, such as a reminder for medication administration or a time log of medication administration, and can hence learn patient response to medications, such as arrhythmogenic drugs, anticoagulants that may alter blood viscosity, or drugs that alter temperature homeostasis. Such corrections are once again useful in minimizing variation in physiological monitoring arising from known perturbations.

A further example of personalized corrections relate to patient posture, such as supine, prone, or angle of inclination, at time of sensing. Some physiological quantities, such as impedance or EKG, are known to be sensitive to posture because of physiological reflexes that may differ between individuals but remain consistent within an individual. Measurements can either be classified by position or otherwise corrected for by empiric learning. Correction for these measures by posture hence enables more consistent ambulatory monitoring where patient position would otherwise render measurements taken in different environments poorly correlated over time.

A further example is the influence of temperature and body fat content on impedance measures. Individuals may have variable correlation between temperature or vasodilation and impedance reading that can be learned over time and integrated into attribute construction to more consistently assess thoracic impedance in heterogeneous environments across time. Body fat content is a similar dependence that can be corrected for, such as by a BMI measure, to personalize an impedance or hydration attribute in health modeling, classification, and prediction. Such BMI correlation may be learned across a patient population, such as by regression, and used in attribute construction to better assess the severity of thoracic impedance changes given an individual's fat content.

Discordance, Timeout, Sampling

Similarly, individual sensors or attributes 412 or 414 may have absolute thresholds that are powerful enough in predictive ability to issue an alert even if other attributes have not yet cumulatively led to a disease classification 418. In such cases of disagreement between sensors at the sensing device stage, a timeout 222 can be initiated to allow for other sensors or attributes to update to maximize predictive power before issuing an alert. The appropriate amount of time for a timeout to minimize false positive rates may be learned as in FIG. 4, such as from initialization 404 or from smartphone questionnaire 406 directed to the sensed individual at the onset of sensor discordance to assess the presence of an acute condition. These methods may also be employed when a sudden change is detected beyond the normal physiological range, suggestive of hardware failure, or if a change is detected that is not yet severe enough to alert emergency personnel but may warrant further scrutiny.

As in FIG. 2, discordance between sensors or attributes can trigger various events 212 and 204 to automatically determine the probability of an emergent condition occurring. One example of such a triggered event is a change in sensing device programming 216, such as an increase in sampling rate to detect any acute changes that may be occurring physiologically to resolve the apparent discordance. For example, if the sampling rate for temperature measurement is less than EKG, a sudden change in EKG may trigger an increase is sampling rate in temperature measurement to validate the EKG finding or suggest another cause for the sudden change, such as hardware failure. This enables health status to be accurately identified while efficiently modulating duty cycle based on sensing need. Another example uses a predefined level of health deterioration to modify such a trigger. While the health status may be insufficient to classify an emergent condition, it may be severe enough to warrant a higher level of scrutiny, such as decreased timeout intervals 222 or increased sampling rate at the expense of memory usage and processing and transmission power. Another example of a trigger is a questionnaire to the smartphone 222 and patient to ensure the discordance is not from mechanical or electrical failure or defect, such as excess sweat or moisture, poor electrical contact, improper device placement, or insufficient electrode distance. The sensed individual may respond to the smartphone notification, such as in the form of an alert 222, to resolve the apparent discordance or sudden change in sensing.

In the preferred embodiment, updates to the smartphone 224 and sensing device 214 are transmitted wirelessly for expeditious response by sensed individual, health care providers, or both. These methods for automatic state evaluation and error-checking may aid in decreasing false positive alerts that are costly to the healthcare provider and may reduce healthcare attention to future alerts.

Baseline Changes Over Time

As patient health or disease changes over the course of long term monitoring, it may be necessary to revise initial baseline values, as represented in FIG. 4, 424. Baseline physiology is known to change in response to chronic conditions, such as from disease improvement or progression. Updating baseline measures is important in longitudinal sensing, such as to prevent false alerts stemming from changes significant to initial baseline but not significant compared to updated baseline. The clinical importance of physiological changes over time depends on factors such as magnitude of change and the attribute itself, and can be best evaluated as increasing data is gathered and processed over time. Processing may take the form of attribute construction 410, weighting by time-since-measurement, or metrics of attribute changes across time, such as percentages or z-scores. Attributes 414 may be well suited to longitudinal evaluation because, depending on construction, may inherently be time characterizations and hence sensitive to baseline changes. For example, an impedance measure may be a z-score calculated over a past time interval of appreciable length and is hence inherently recalibrated to a new baseline as time progresses. Such correction is useful, for example, if a sensed individual has progressive dissolution of pulmonary edema after discharge and must have their new thoracic impedance baseline updated to better detect future incidences of fluid retention.

Weights used to update baseline changes may also be learned and personalized, such as by patient feedback through smartphone questionnaires 406. Because of the biological variability of individual response to chronic change, patient reporting may be used to enhance attribute construction, such as by mutual validation. Examples of patient reportable chronic changes to validate computed quantities include orthopnea, pedal edema, or decreased exercise capacity.

Windowing

Figure 10:
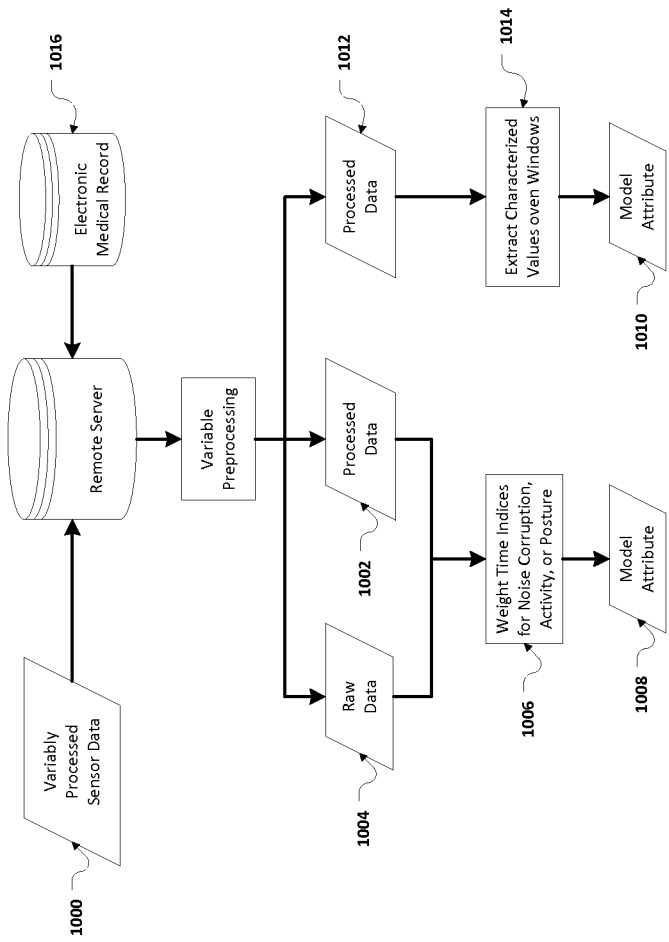
FIG. 10 shows a process for using time interval windows of a larger data set to weight data, such as by noise level, or to produce a characteristic value of the time interval for use in attribute construction.

While some physiological quantities necessitate continuous or substantially continuous monitoring for detection of acute changes that may require immediate intervention, such as ventricular arrhythmias, other pathologies follow more indolent courses whose progression can be more accurately evaluated by selectively analyzing periods of data that are least corrupted by noise. FIG. 10 presents a preferred implementation in which data from one sensor 1002 provides information on noise level to window simultaneously recorded data from another sensor 1004, to restrict processing of data 1004 to windows that are minimally contaminated by noise, such as by weighting 1006, to yield a robust model attribute 1008.

Windows can also be used to construct characteristic attributes 1010 of data over a time interval derived from a larger data set 1012. Examples of values computed 1014 from a windowed interval include, but are not limited to, measures of central tendency, dispersion, time duration in a given state, rates of change, areas under the curve, spectral profiles, phase comparisons, maximum or minimal values in the time or frequency domain, or normalized values, such as percentages, z-scores, or other changes with respect to maximum or minimum, baseline, or other present or past values. These characteristics can be obtained from window lengths that are static or dynamic and may be further combined for generalizing sensor data over extended time intervals, such as days, weeks, or months. In embodiments where windows are not continuous throughout a time series, separations or gaps may be corrected for by extrapolating historical trends.

Artifact Removal and Preprocessing

Cross Sensor

Using multiple coincident recordings not only enables attribute construction from corrected, mutually validated, or otherwise fused sensor outputs but also enables noise detection for correction in attribute construction and duty cycle reduction in high noise states at the sensing device stage.

Figure 11:
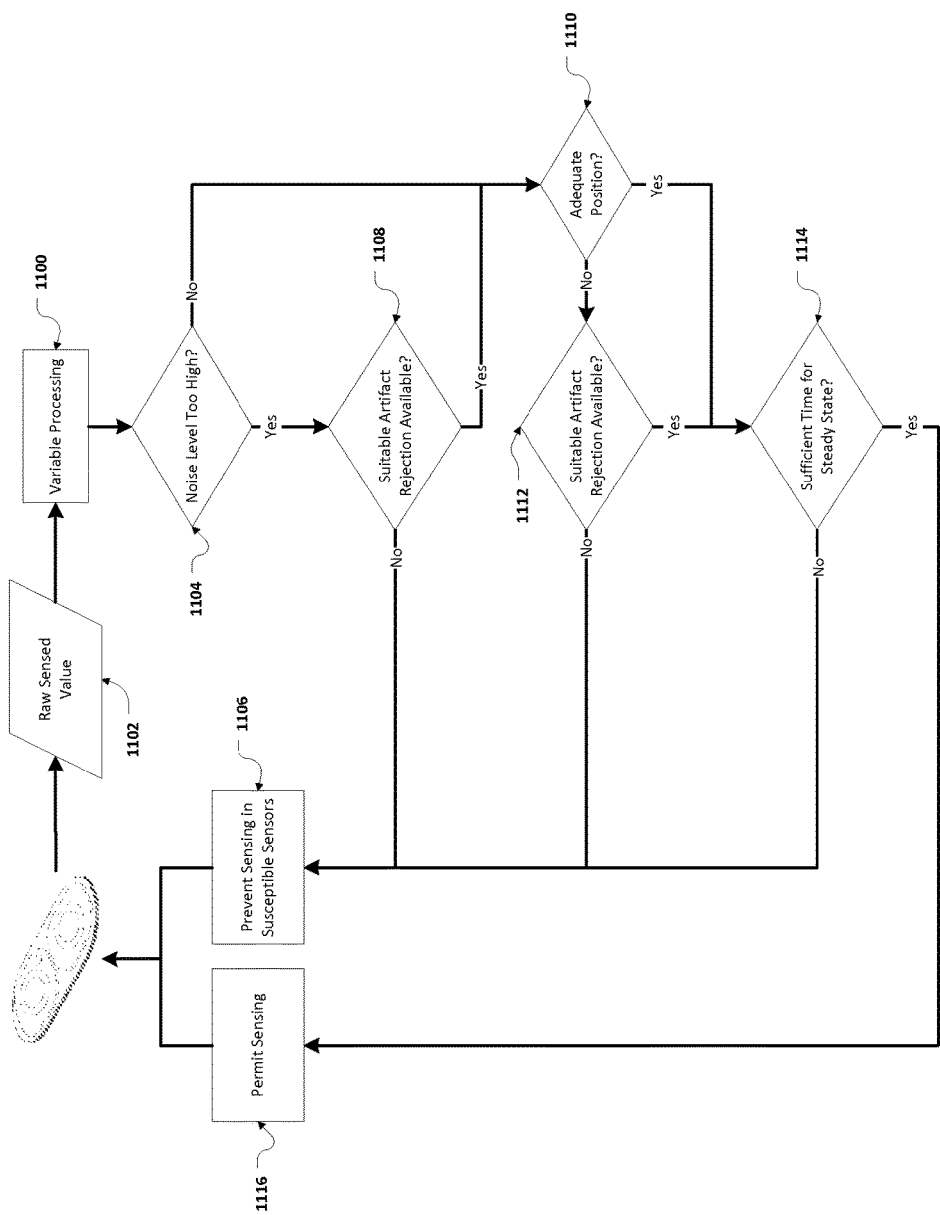
FIG. 11 shows a process for noise gating at the level of the sensing device such that sensor duty cycle may efficiently be controlled depending on noise level.

As in FIG. 11, power and memory can be conserved in the sensing device by using system noise characterization and processing from other sensors to prevent the sensing, processing, storage, and transmission of noise corrupted data, such as during movement, the lack thereof, or a particular position impeding full dynamic range of physiology or sensor recording. If processing 1100 of sensed quantities 1102, such as from the accelerometer signal, reveal an elevated noise level 1104, then further sensing by susceptible sensors may be blocked 1106 depending on the ability of downstream artifact rejection to correct for the noise level or type 1108. Similarly, if the sensed individual's position does not provide ideal measurement 1110, further sensing by susceptible sensors may also be prevented 1106 if adequate artifact rejection is not available 1112.

It is also appreciated that time must pass after the offset of a high noise or specific posture state before the measurement environment returns to steady state. Such a time constant may be accounted for 1114 before allowing sensing to proceed again 1116.

The reduced duty cycles may resume to normal, such as when the noise level has returned to an acceptable level and sufficient steady state has been reached 1116 with the benefit of reduced power and memory usage in the preceding high noise sensing state. For the purposes of the described method, noise level may be characterized in many ways, such as RMS, duration of RMS level, average rate of change over time of RMS or envelope, area under the curve of envelope, or combinations thereof across one or more axes.

Past the sensing device stage, coincident sensing of activity level and posture allows for downstream correction of changes that are known to influence readings of sensors such as EKG, impedance, phonocardiogram, or temperature. For example, if the activity signal is known to exhibit strong activity in a certain spectral band that is apparent in other sensors and is uncorrelated to known or relevant physiologic phenomena, artifact removal techniques known in the art, as detailed in patent application US20080045815 that is hereby incorporated by reference in its entirety, and may be implemented prior to processing the contaminated signal for minimal downstream disruption, such as in FIG. 10, 1006.

A further example allows for weighting of measurements taken during noise corrupted intervals as determined by measurement from other sensors, as in FIG. 10. Examples of such noise corrupted periods may include heavy exercise, which may influence temperature and impedance, or eating and drinking, which may influence breathing pattern. Data collected in these periods may be corrected by activity level with mathematical operations such as ratios with characteristic physical activity values described earlier.

Other examples of noisy environmental states may be external to the individual and may include sudden encounters with other individuals, transportation, convulsions, or any other movements that might occur in daily activity that may or may not be medically relevant. While such noise may contaminate other sensors, it may also provide valuable clinical information, such as the presence of seizures or a fall, and may trigger alerts in the fashion of FIGS. 2, 208 and 204.

A further example of downstream correction involves classifying quantities by environmental state, such as measures known to be dependent on posture, angle of inclination, or while supine or prone, such as thoracic impedance. The continuous or substantially continuous recording of activity and posture enables classification of such measures by activity level or posture and may be integrated during attribute construction. For example, a measure of thoracic impedance may be used to construct multiple attributes depending on posture at the time of measurement, such as impedance at 30 degree incline, impedance at 60 degree incline, etc. Another example is the use of a correction factor in attribute construction, such as a ratio of impedance reading and degree of incline.

In another example, organ function may appear diminished in a patient because of their current activity or environment though they may not be in or approaching an emergent state. As an example, heavy activity may reduce the heart's ability to fully perfuse the myocardium in a state of stable angina that does not require immediate intervention or care. Such health characteristics may be corrected for by the simultaneous activity level.

In another example, ectopic heart beats are phenomena known to be detected in EKG and can disrupt data processing. Ectopic beats can occur in various contexts, such as in movement, physiological ventricular beats in diastole, as detailed in U.S. Pat. No. 8,137,270 that is hereby incorporated by reference in its entirety, premature ventricular contractions (PVC), uncorrelated beats, electromyogram (EMG), or electromagnetic interference (EMI), and may be accounted for with the simultaneous activity recording.

In another example, heart rate variability (HRV) measurement may be distorted by interference with autonomic control, such as from aging, or by dynamic breathing patterns, such as periodic breathing (PB) or Cheyne-Stokes, through the effect of respiratory sinus arrhythmia (RSA). Monitoring and classification may be improved by correcting for these parameters. For example, weights may be assigned to correct for patient information, such as age, gender, or health state, or by using coincident data obtained from another sensor, such as an accelerometer, that characterizes and correlates respiratory function, body position, or sleep status.

Cross Time

Figure 12:
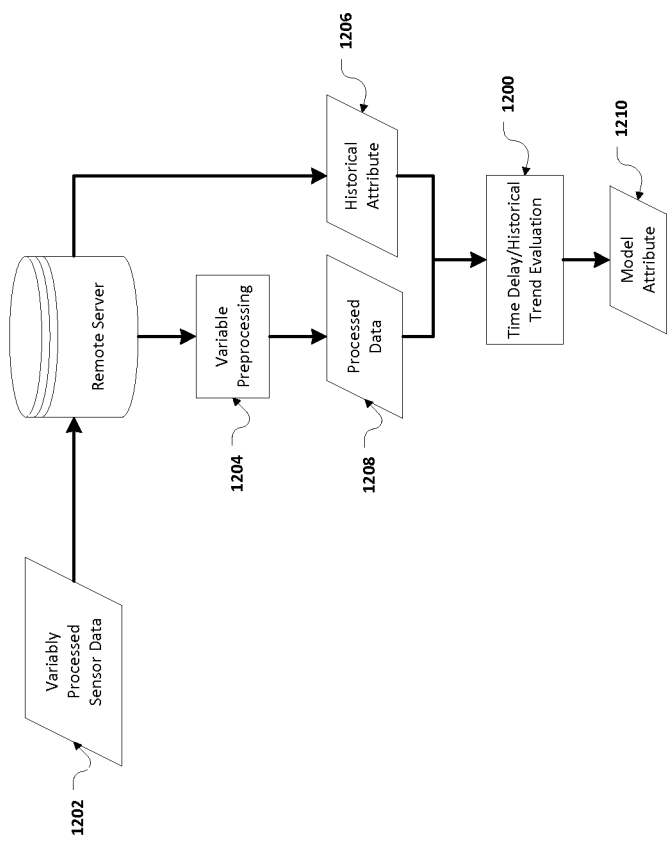
FIG. 12 shows a process for attribute construction by combining current data with historical data stored in the database on the remote server.

In addition to inter and intra patient variation, physiological quantities may exhibit non-significant fluctuations over time or from sensing artifact and may be corrected for to improve accuracy of monitoring and classification. As in FIG. 12, particular embodiments may incorporate hysteresis in attribute construction 1200, such as a time delay. As current data 1202 is received by the remote server for further processing, data may be variably processed 1204 before comparison with historical attributes stored in the database 1206. The past attribute 1206 and present data 1208 may then be combined 1200, such as by comparing time past threshold, rate of change, or severity of subsequent action, to construct an attribute 1210 for eventual input to the health state classification model.

This time delay factor may thus prevent non-significant fluctuations in measurements from triggering false alerts. Because of biological variability, the time delay attribute construction 1200 may be learned from fluctuations occurring during an initialization period or from smartphone questionnaire FIG. 4 that can determine the appropriate time delay to distinguish transient fluctuations from true disease onset. As an example, the time delay may be included in attribute construction 1200 as a weight dependent on factors such as time-since-last-threshold-crossing, number of past threshold crossings per unit time, interval of time spent past threshold, raw or normalized magnitude of change past threshold, or outlying distance from central tendency or dispersion.

If a patient's threshold is being adjusted or learned in a region dependent on past values, a timeout can be initiated and satisfied before the threshold or value is updated to ensure that a recurrent phenomenon is not continually misclassified. This may be done at any system stage, such as at the sensing device level 222 or at the remote server level 1200. A timeout may be dependent on the specific physiological quantity being sensed or derived with relation to time stamps, as detailed in U.S. Pat. No. 6,336,903 that is hereby incorporated by reference in its entirety, the severity of the implied condition, or any other attributes of the patient's history or past monitoring.

Hysteresis may also be a physiological factor where a specific phenomenon depends on the past state. For example, some EKG rhythm patterns may be dependent on past heart rate, such as repolarization alternans hysteresis during recovery from elevated heart rate. The above methods may hence be used to accurately identify and classify such an arrhythmia burden as an attribute, as well.

General

The ambulatory nature of remote monitoring introduces various noise sources. These may be random in nature and temporal occurrence or may be structured and susceptible to artifact rejection. Many methods may be used to maximize the usefulness of data subject to noise that may be present continuously or substantially continuously.

Outlier data points may result from an underlying electrical, mechanical, or physiological source and can be removed in early processing to prevent corruption of downstream processes. The removed points may be replaced by extrapolation of near neighbors, historical trends, or patient information. If the point is not replaced and other data streams require alignment, sampling rates may be modified to allow for further processing. If the outlier is part of a larger cycle, the entire cycle may be removed from all but the minimal amount of downstream processing required. The specific method depends on the sampling frequency required by the involved physiological attribute being measured that is in turn dependent on the physiological dynamic range. In the preferred embodiment, the smartphone may be used to automatically inquire regarding possible noise source, as in FIG. 2 222.

As an example of outlier data processing, filters may be used to remove EMI from nearby power sources. As a further example, filters of varying notch frequencies or rectification may be used to clean the spectrum and may aid in distinguishing phenomena that may have similar spectral components.

Data Transmission

Data transmission allows for disseminated computation to maximize specialization of each step in the health and disease monitoring system. Furthermore, the smartphone FIG. 1, 110 is used as a preferred intermediate step in data transmission to decrease power consumption of the sensor device 100 and enrich the data by adding further information 138 from the individual to aid in monitoring and state classification 130. Furthermore, the smartphone utilizes existing cellular architecture to minimize the need for proprietary hardware in this system to reduce structural barriers to clinical implementation and adoption. Furthermore, the wireless transmission medium between sensing device 100 and smartphone 110 by 136 does not require supervision by the sensed individual to allow for increased ease of use. The wireless medium also allows for more continuous monitoring as the device need not be removed for transmitting data, such as by a cable to computer or modem.

Data is sampled continuously or substantially continuously for physiological quantities necessitating such sample rates, while other quantities known to change more slowly are by default sampled less frequently. As in FIG. 2, sampling rate can be overridden 216 for each sensor for a variety of reasons, including triggers initiated by the sensed individual 206, physiological system 208, or healthcare provider 202. In restricted power settings, sampling may be further altered to conserve power for critical measurements that may change acutely and require immediate response. Subsequently, the system of disseminated computation allows for processing to occur at a variety of levels, such as at the stage of sensing device 226, intermediate device 228, such as smart phone, or at remote server 230.

The sensing device can be instantiated with a default transmission schedule for transmission from sensing device 226 to smartphone 228 to balance power consumption with clinical timeliness. The default schedule can be altered by a variety of methods as in FIG. 1. The schedule can be manually programmed by a physician or caregiver 202 for a variety of reasons, such as to increase or decrease transmission frequency or change transmission schedule. The default schedule can be overridden if sensing device memory is full 230, such as from prolonged lack of signal between sensing device 226 and smartphone 228, as may arise from loss, misplacement, or forgetting of smartphone, battery depletion of the smartphone, or smartphone hardware problem. The default schedule can be overridden by the patient for a variety of reasons, such as in event recording usage 206. The default schedule can be overridden in the context of an alert state issued by the device 208, 210, such as in response to sensor discordance 212. The detection of certain physiological entities indicative of acute processes may also prompt immediate transmission to smartphone 208, such as a lethal arrhythmia, for automated alerting 234 of emergency services.

Smartphone Gathered Data

In the preferred embodiment, the smartphone 110 is used as an intermediate data transmission device. This enables the use of the smartphone to gather further information to improve monitoring, such as social interactions 138.

As an example, the smartphone may be used to measure patient compliance as a feature, as described previously. As a further example, the smartphone may be used to assess patient reported information through a questionnaire feature. Said function may be used in initialization as described earlier FIG. 4. Examples of such items include quality of life, energy level, or exercise tolerance. As a further example, if the GPS function is enabled on the smartphone, a geographic location may be determined and used to assess distance from healthcare facilities.

Therapy Guidance

As in FIG. 1, a preferred embodiment may use the smartphone to monitor the effects of therapeutics 126, especially those with cardiac, pulmonary, or autonomic nervous system side effects. Physiological monitoring may not only guide patient treatment by a healthcare team in dosage titration but may also be used for research purposes 128 to improve therapies with knowledge of potentially subtle therapeutic effects.

As an example presented in FIG. 4, some drugs may carry arrhythmia warnings and with knowledge of administration times, such as from a smartphone log 426, drug effects may be evaluated using the continuous or substantially continuous EKG signal. As another example, some drugs may carry side effects relating to temperature homeostasis and may be evaluated similarly. Such effects may be corrected for in the process of attribute construction 414 to enhance model performance by correcting for fluctuations in longterm monitoring.

Acoustic Signal

Figure 13:
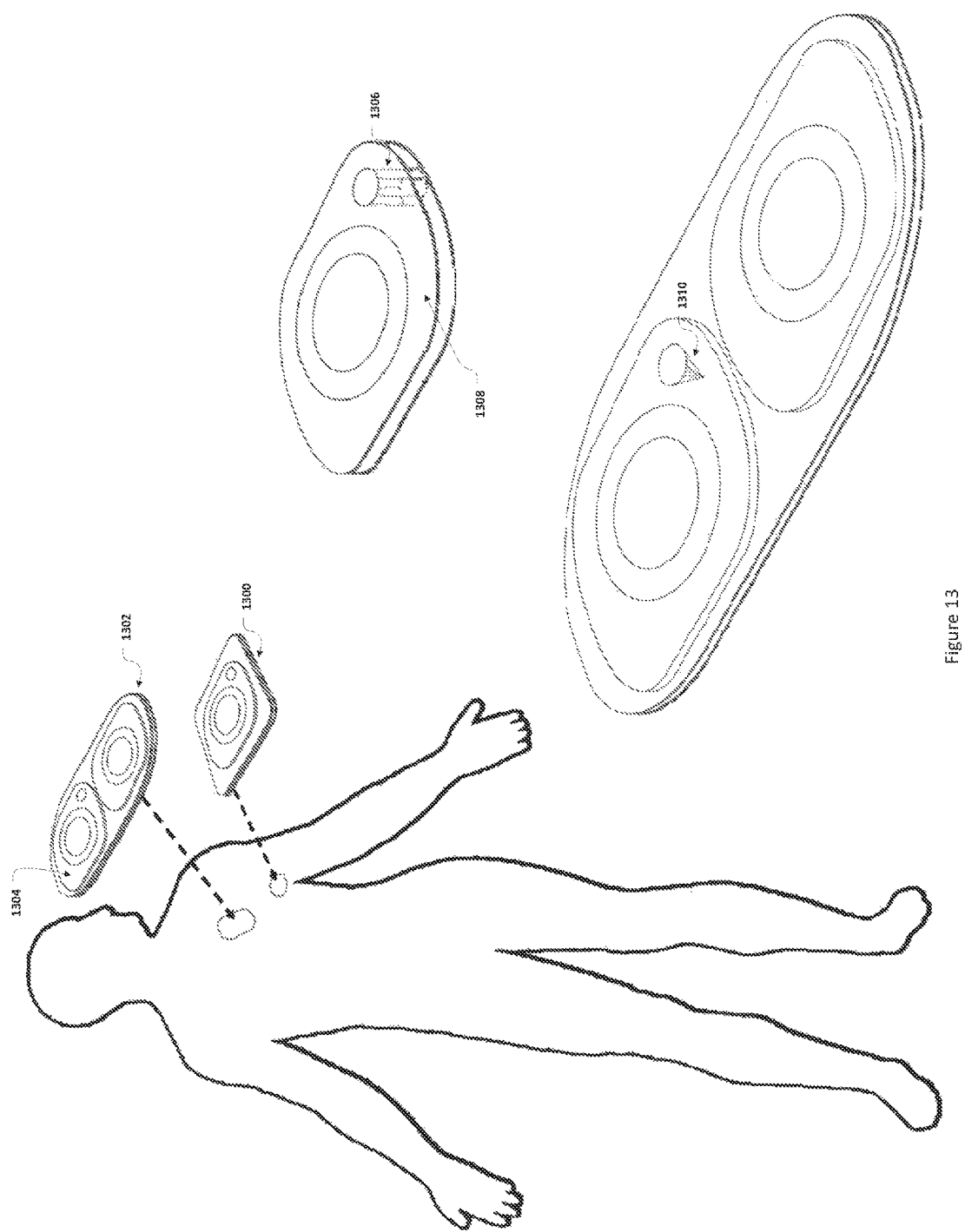
FIG. 13 shows an embodiment of the adherent patch sensor, a satellite extension of the primary sensor, and a schematic of the hardware specialization of shared electrode leads to collect EKG and impedance data and the airflow configuration to collect acoustic data from the torso with enhanced amplification and noise isolation.

In a preferred embodiment FIG. 13, the sensing device 1300 carries one or more microphones with a direct air or diaphragm contact to the chest wall for the detection of acoustic signals arising from mechanical movement within the thorax. Cardiac and pulmonary acoustic signals can provide insight into health or disease status. The different spectral profiles of cardiac and pulmonary signals enable isolation of acoustic signals by origin and use in monitoring and disease prediction.

To improve acoustic signal sensing in the minimal space provided at the sensing device stage, the microphone acoustic contact with the thorax may be integrated with the existing electrode pad 1304. Electrode pads may have an adhesive contact with the skin and are firmly attached to the sensing device. By boring a hole 1306 in the non-conductive portion 1308 of the traditional pad, a relatively continuous and isolated column of air may be provided to connect the skin with an acoustic sensor on the sensing device. Both the primary adhesive patch and the satellite patch may have similar configurations to allow for this method of acoustic sensing. To further enhance amplification, a funnel 1310 may be used on either or both patches to increase acoustic pressure as air travels through the column between skin and microphone sensor. Depending on the application and desired frequency range sensitivity, a diaphragm may be used, such as to detect higher frequency pulmonary sounds, or an open bell may be used with the skin acting as the diaphragm in the detection of lower frequency heart sounds.

If the acoustic noise in the sensing environment overcomes the acoustic insulation provided by the pad in 1306, a variety of sensing device and downstream processing algorithms may improve sensing, such as by reducing duty cycle in noisy environments, enabling recording in ideal environments, or filtering data to remove noise corruption or repetitive patterns. For example, the slow progression of acoustic changes and the continuous or substantially continuous sensing by the adherent patch enable acoustic signal recording or processing to be restricted to time intervals of low acoustic noise without sacrificing classification or prediction performance.

Furthermore, the use of multiple acoustic sensors allows for data mining techniques to identify individualized sensing parameters that are difficult to predict a priori, such as by using independent component analysis. Such techniques may also be supplemented with other non-supervised methods, such as k-means clustering, to identify personalized patterns such as optimal frequency of heart or lung sounds or spectral profiles distinguishing individual sounds, such as S3, S4, or crackles from other noise sources. These results may then be correlated to health state and constructed as an attribute for classification.

Heart Sounds

Traditional heart sounds can be obtained from both chest-worn microphone and accelerometer and validated with coincident recordings from other sensors, such as the EKG. Heart sounds are known to have a spectral peak below 200

Hz and can be decomposed with time frequency decomposition techniques for characterization of heart function. By using multiple sensors for acoustic signal detection, signal estimation may be enhanced throughout the course of ambulatory monitoring where the physiological system or environment may introduce significant noise, as in FIG. 11.

Furthermore, acoustic signals may be used to validate data from other sensors or be constructed as attributes for health or disease monitoring or classification, as described in FIG. 9. As an example, heart rate may be determined or validated with other sensors by measurement of a periodic entity, such as the S1 heart sound that may be obtained from the accelerometer, microphone, or both for increased accuracy by mutual validation. If the S1 sound is poorly appreciated for any reason, such as the location of the sensing device on the torso, any other periodic heart sound may be used, including S2. Use of a prominent mechanical signal, such as the S1, also serves for alignment with other physiological phenomena, such as the heart's electrical activity or pulmonary function.

A further example uses heart sounds to improve estimation of respiratory rate by using the characteristics of change in distance from sensor to movement origin as a surrogate for respiratory chest movement. The change in intensity of heart sounds, such as S1 or S2, may be accurately identified after operations including filtering, enveloping, or aligning with corresponding sensors, such as EKG, to measure changes in signal magnitude over a window of time of sufficient length to capture a desired number of respiratory cycles. The heart rate often satisfies the Nyquist sampling rate necessary for respiratory rate estimation in states of both health and disease, as detailed in patent application US20110021928 that is hereby incorporated by reference in its entirety.

A further example uses the alignment of the mechanical and electrical heart signals to allow for improved identification of signals suggestive of pathology, such as the S3 or S4 heart sounds. Due to the random introduction of noise from daily ambulatory activity, microphone or accelerometer data may not provide a continuous data series with the desired level of physiological quietness. This may be corrected for by selection of data windows with minimal noise corruption, such as minimal movement as detected by the accelerometer characterized by RMS, duration of RMS level, average rate of change over time of RMS or envelope, area under the curve of envelope, or combinations thereof across one or more axes. Even in settings of low noise, performance may be enhanced by alignment with sensors less susceptible to similar noise events, such as the EKG. This allows for temporal restriction in the identification of S3 or S4 heart sounds because of the known temporal relation between mechanical and electrical activity.

In preferred embodiments, heart sound identification may be further enhanced by personalizing thresholds to account for patient variability. Initialization periods may be used, for example, to train learning algorithms to the proper threshold of detection and heart sound characteristics personalized to an individual, as in FIG. 4. Through any such methods, a personalized heart sound attribute may be constructed and submitted to the classification system.

Lung Sounds

Respiratory function is manifested acoustically at higher frequency bands, between 100-1000 Hz and may be evaluated for the presence, absence, or severity of lung sounds as attributes that may guide health or disease monitoring or classification. Examples of such sounds include rales or crackles and are known to be indicators of deteriorating lung or heart function. Time frequency decomposition techniques described earlier have been shown to separate these physiological phenomena based on their distinct spectral profiles. As with heart sounds, personalized thresholds may increase accuracy by learning from empiric patient data obtained during an initialization period FIG. 4. Time and frequency components from the acoustic signal may be combined in a cross-validation or stacked generalization system to combine these attributes for enhanced detection of lung sounds, such as crackles.

Furthermore, information from body position may be used to enhance data obtained from lung acoustic signals because of the dependence of hemodynamics on body position and gravity FIG. 11, 1110. A failing heart will have increasing difficulty pumping blood against gravity as the force vector counteracts the pumping force. As such, pulmonary findings in diseases such as heart failure can be position dependent and may thus be further quantified as an attribute by using coincident information from the accelerometer. For example, the presence of crackles may be due to mild heart failure if the individual is supine in a reclined position. However, advanced heart failure may result in crackles occurring while upright with minimal gravitational resistance. As such, simultaneous recording may add more information to recorded data and enhance classification.

Accelerometer (Activity Signal)

A preferred embodiment of the chest worn sensing device includes an accelerometer that is able to detect movement of the chest wall in one, two, or three axes. To minimize the total size and complexity of the sensing device, a single adherent patch 1302 may record accelerometer signals to facilitate ease of device attachment for the goal of increased patient compliance throughout longterm monitoring. This serves in contrast to other movement sensing methods, such as respiratory inductance plethysmography, that depend on a difference between multiple sensors to estimate respiratory function, such as tidal volume or respiratory rate. These cumbersome devices are avoided in the presented invention by specialized disseminated processing to uncover respiratory function from a single accelerometer and mutual validation with other sensors, such as the EKG or one or multiple microphones. Though a second patch 1300 may be used if body habitus precludes accurate sensing of other physiological signals as described earlier, this is not required in the present invention to accurately model or classify health state or predict emergent conditions. The accelerometer signal may be used to characterize multiple physiological parameters, either individually or in combination with other sensors on the device with variable sampling frequency.

As an example, general activity level may be determined through various transformations of the one, two, or three dimensions, such as RMS, duration of RMS level, average rate of change over time of RMS or envelope, area under the curve of envelope, or combinations thereof across the one or more axes.

The structure of such characterizations, such as central tendency and dispersion, may then be classified by comparison to known activity profiles, including but not limited to walking, running, or jumping. Such state classification may then be used in attribute construction for classification of health and disease state or used to derive further parameters, such as by sensor fusion. As an example, activity data may be fused with EKG derivatives, such as heart rate or HRV, to serve as a surrogate clinical stress test. As a further example, time information may be used to quantify the amount of time spent walking in a 24 hour period to form an attribute representative of fitness level or conversely disease burden.

Further information may be derived about movement from the accelerometer signal. As an example, walking pattern may be estimated by the spectral profile in one or more dimensions of acceleration and deceleration. As a further example, aspects of movement may be further derived, including stride length, angle, or speed. General and more specific activity levels may be indicative of health state and useful for longitudinal monitoring in chronic diseases that may slowly or subtly impair activity and movement preceding the onset of an emergent condition.

A further example is the determination of posture from an accelerometer. In multiple dimensions, posture may be determined by the relative strength of acceleration in different directions. Posture can be determined while at rest or during movement and may offer insight to health monitoring from the characteristics of daily activity movement, such as posture while ambulating. Furthermore, these quantities may be used to increase consistency among sensed quantities and model attributes by temporally restricting processing to intervals of specific sensing conditions, such as a given posture or activity level.

A further example uses movement information from the accelerometer with or without GPS information from the smartphone to map activity and movement. The relationship between acceleration, velocity, and displacement allows acceleration data to estimate distances traveled and speeds, such as for use in exercise. If a smartphone has GPS capabilities available and enabled, information may be validated with the GPS and augmented to include geographic information that may show trends in activity reflective of underlying physiology and informative to health or disease monitoring or classification.

A further example may use the chest worn accelerometer to characterize mechanical hemodynamic function as an attribute. The magnitude of displacement during the cardiac cycle is known to correlate to acoustic and electrical activity as described previously, and may be used to validate other signals for improved accuracy in times of increased noise. For example, S1 and S2 heart sounds are known to have mechanical correlates that may be used to measure heart or respiratory rate, in addition to the EKG or chest excursion, as explained previously. Furthermore, the S1-S2 interval has a known physiological link to respiratory rate and may be correlated for mutual validation to improve accuracy given the size restrictions of the adherent patch and high noise environments. Heart sound magnitude may be quantified in many ways, including peak or peak-to-peak amplitude, area under the curve, duration, or any other number of operations.

The magnitude of heart movement is also known to vary in different states of health and disease, such as decreased apical impulse magnitude by a weakened myocardium, and may be trended over time for characterization and classification. The impulse results from the rotation of the myocardial muscle during contraction and the impulse of the apical thrust against the chest wall is thus dependent on posture, such as position behind a rib. As such, preferred embodiments may weight apical impulse magnitude in attribute construction with information including position, incline, laterality, or posture, to improve longitudinal performance of the input attribute or feature. Furthermore, placement of the accelerometer sensing device near the midclavicular aspect of the fourth and fifth ribs best allows for detection of this signal.

Furthermore, changes in apical impulse may correlate to strength of heart contraction. The strength of S1 and S2 heart sounds is also correlated to the force of blood passing through heart valves, and both measures may be combined to estimate changes or trends in blood pressure given an initialization 404 or other training examples, such as physician visits 408, as presented in FIG. 4. Blood pressure is multifactorial, however, and is modulated by other mechanisms, as well.

A further example of accelerometer data use is for chest excursion. The chest is known to move with the frequency of respiration and may be separated from other mechanical influences for determination of tidal volume and respiratory rate. Due to the continuous or substantially continuous nature of recording, sampling may be favored in times of reduced movement or preferred body position 1110, such as non-prone, to minimize noise corruption of the low frequency respiratory signal while faithfully characterizing longitudinal trends in the individual's respiratory rate and function. Furthermore, as discussed previously, respiratory rate may be validated with other physiological parameters, such as RSA and dynamics of heart sound magnitude or intervals. The independent tests used to validate higher order attributes, such as respiratory rate, may be combined using averages, weights, voting schemes, cross-validation, or stacked generalization to identify the most accurate measure for a sensing device type or to obtain an ensemble measure with improved performance.

A further example uses accelerometer data to validate other sensed and derived physiological quantities with general movement. For example, early coronary artery disease may only manifest symptoms upon exertion, termed angina of effort or stable angina. As such, in pathologies such as heart failure, symptoms of decompensation during exercise without manifestations at rest may necessitate less intervention than decompensation occurring at both exercise and rest.

A further example of accelerometer use is in determining the background noise level from the physiological system or environment, as in FIG. 11. For example, moderate to intense activity may alter hemodynamic, respiratory, or temperature homeostasis and preclude sensing of resting state physiological quantities that are useful for some input attributes. Environmental causes may include vibration from transportation. By using the accelerometer as a noise level gate, power and memory may be conserved by preventing unnecessary measurements that may not benefit the health monitoring or classification system, such as impedance, accelerometer derived respiration, or phonocardiogram. Other quantities may benefit from movement by offering a greater dynamic range to be measured by the physiological system with correction operations, such as normalization by activity level. Examples include changes in heart rate, respiratory rate, or temperature in response to activity or recovery. As an example, the 6 minute walk test offers a clinically useful characterization of heart function in individuals suffering from heart failure. Due to the continuously or substantially continuously monitoring of the present invention, an appropriate surrogate test may be extrapolated by comparing time intervals of movement, such as walking, with cardiopulmonary attributes, such as heart or respiratory rate, as outlined in FIG. 9. Further examples of attributes dependent on physical movement include EKG changes that become apparent with dynamic heart rate. Such examples include TWA and QT hysteresis, as detailed in U.S. Pat. No. 6,671,549 that is hereby incorporated by reference in its entirety, that may be variably expressed depending on increasing, decreasing, or stable heart rate and can be assessed using the coincident and continuous or substantially continuous recording of the accelerometer and EKG in the preferred embodiment.

As in FIG. 2, a further example of accelerometer data is in the characterization of pathological movements or other emergent conditions detected at 208 and sent to remote server 230 for detection of the state 236. Some emergent disease states may involve sudden physical changes that may trigger an alert 204 for immediate intervention, such as a smartphone questionnaire or alert 222, hospital visit, or healthcare team alert 232. Examples of such states include seizures, falling and requiring assistance as in the case of the elderly, or falling from a syncopic episode that may derive from hypoglycemia, neurogenic syncope, heart attack, or stroke.

FIG. 2 presents a preferred embodiment where the accelerometer data is used to monitor activity level against a goal for exercise activity in a time interval. For example, an individual, such as an athlete or patient, may be advised to sustain exercise, characterized by attributes such as activity level, heart rate, or respiratory rate, for an indicated amount of time. The smartphone 228 may thus be used to notify the user of remaining duration, if any, of recommended exercise 238. Signs such as heart or respiratory rate may be monitored warming up, during exercise, and while cooling down, as detailed in U.S. Pat. No. 8,140,154 that is hereby incorporated by reference in its entirety.

A further example includes the use of monitoring preferred sleep position. In some disease states, such as heart failure, patients tend to avoid certain positions because of discomfort. For example, paroxysmal nocturnal dyspnea is known to disrupt sleep in patients who succumb to hydrostatic leak of fluid into their lungs and may wake while sleeping with anxiety, dyspnea, coughing, or other symptoms. Such individuals who may have symptoms of orthopnea learn to sleep with multiple pillows at night, a subtle change that may be monitored by degree of inclination by the accelerometer during periods of sleep that may also be coincidentally detected by the accelerometer. Heart failure patients have also been found to avoid the left lateral decubitus position while sleeping, believed to be a result of increased heart size and sympathetic stimulation, a change that is readily identified during sleep with continuous or substantially continuous recording to derive sleeping position. Similarly, episodes of trepopnea may be detected and classified for better characterization of patient discomfort arising from pathological disturbance.

Temperature

A preferred embodiment of the sensing device includes a thermometer to measure body surface temperature. The thermometer may take many forms, such as a thermistor, IR temperature sensor, or thermocouple. Temperature is known to be modulated by physiological and pathological processes and may be useful in longitudinal health monitoring, such as in heart failure. While measurement of external skin temperature may not be identical to axillary, rectal, oral, or tympanic membrane temperature readings, the presented invention's method of specialized disseminated processing enables correction for the sensed values and correlation to clinical temperature readings while maintaining a non-invasive and easily applied adherent patch sensor for ease of patient use and compliance.

To correlate the sensing device 402 external temperature reading as described above, a supervised learning method may be used as in FIG. 4. Verification of the temperature state 420 may be performed with gold standard measurement 428 and learned based on the sensed individual's response using a variety of supervised learning methods FIG. 5, such as regression or the perceptron algorithm.

Skin temperature may be affected by cutaneous vasodilation and may offer an important correction term for the impedance measurement that may record lower impedance than in non-vasodilated states. As severe disease states, such as heart failure, affect the hydration of deeper tissues, such correction in attribute construction may be used to prevent false alerting.

Temperature is also known to fluctuate with sleep/awake cycles and may be used to mutually validate sleep state with accelerometer derived activity level characterization. Temperature is also modulated by a circadian rhythm throughout the day. Subject to biological variations like many other quantities, such rhythmic temperature changes may be personalized to patients by using empiric historical data to better characterize and correct for temperature baselines and thresholds, reflected by attributes containing these corrections. Supervised FIG. 4 or unsupervised learning methods may be used to identify individual patterns or classify states as normal or abnormal with personalized thresholds to provide correction factors to attributes for the health and disease state model.

The above correction methods improve longitudinal surveillance by providing consistent temperature reflections across time with reduced susceptibility to fluctuations, such as by physical activity or circadian rhythm, that may otherwise decrease modeling, classification, or prediction performance.

Temperature measurements may be run on a default schedule as described above to balance power consumption with data acquisition. This balance is influenced by the chronic nature of heart failure in which temperature changes may take days or weeks to occur and hence may not require continuous or substantially continuous sampling. For example, in the default setting, sampling may be restricted to 25 or 50 times per day spaced in 5 to 10 clusters, where the intracluster time interval is much shorter than the intercluster time interval.

Clusters may be characterized by a variety of means as described earlier 1014, such as normalized or non-normalized metrics of central tendency and dispersion, rate of change, area under the curve, differences, or duration past threshold and may be used to construct attributes for the monitoring system. The readings may be windowed with static or dynamic length, or with variable overlap, as described previously. Windowed values may be further combined, such as by averaging, over extended periods of time, such as 6 or 24 hours or longer. Characteristics of these extended windowed combinations, such as measures of central tendency, dispersion, magnitudes, or rates of change, may also be used as attributes 1010 in monitoring and classification.

A preferred embodiment may use other sensors on the device to correct for temperature changes not due to an inherent or autonomous physiological or pathological process. For example, degree of physical activity may alter temperature and hence may be corrected for using coincident measurements, such as from the accelerometer's activity attribute. However, magnitude of temperature response during and recovering from activity, such as slope of 500, may be used as its own attribute classified by activity state and trended over time for health monitoring or classification through any of the methods described previously.

A further example includes the effect of medication or food on body temperature to evaluate subtle effects from such therapies. The questionnaire or logging function of the smartphone 426 may be used to provide a time stamp for monitoring such changes.

It is understood that temperature responses to stimuli, such as medication or physical activity, may have a lag time to peak effect, and, as made possible by dynamic sampling, may be accounted for by automatically or manually adjusting sampling time or weights in response to event occurrences.

Impedance (Hydration Signal)

A preferred embodiment includes electrodes capable of sensing the impedance between the contact pair. The pair may be shared with the EKG lead to minimize the sensing device size and increase patient long term comfort, as described previously.

One of the compensatory methods of the body for maintaining tissue perfusion in states of weakened myocardium is increased intravascular volume, as greater volume increases the pumping ability of the heart by the Frank-Starling relationship. However, the increased volume load eventually results in fluid accumulation in the body, a physiological state known to manifest as reduced electrical impedance as measured across the thorax.

While impedance may be used to detect hydration or hemodynamic changes as blood is pumped throughout the thorax, at significantly lower sampling rates it may also serve as an indicator of fluid retention with substantially decreased power requirements. While heart failure may result in excess fluid throughout the body, an early sign of left sided heart failure is a buildup of fluid in the lungs. In the preferred embodiment, the two electrodes of the device may evaluate for changes in impedance across a variable distance, such as the length of the sensing device, which may be on the order of inches.

Impedance measurements may be run on a default schedule as described above to balance power consumption with data acquisition. This balance is influenced by the chronic nature of heart failure in which fluid retention may take days or weeks to occur and hence may not require continuous or substantially continuous sampling. For example, in the default setting, sampling may be restricted to 25 or 50 times per day spaced in 5 to 10 clusters, where the intracluster time interval is much shorter than the intercluster time interval.

Clusters may be characterized by a variety of means as described earlier 1014, such as normalized or non-normalized metrics of central tendency and dispersion, rate of change, area under the curve, differences, or duration past threshold and may be used to construct attributes for the monitoring system. The readings may be windowed with static or dynamic length, or with variable overlap, as described previously. Windowed values may be further combined, such as by averaging, over extended periods of time, such as 6 or 24 hours or longer. Characteristics of these extended windowed combinations, such as measures of central tendency, dispersion, magnitudes, or rates of change, may also be used as attributes 1010 in monitoring and classification.

In a preferred embodiment FIG. 11, impedance sensing may utilize coincident accelerometer sensing to gate and classify measurements to prevent unnecessary sensing and reduce power and memory requirements for improved device comfort and compliance in longterm monitoring. This may be advantageous in preventing sensing in times of high noise, such as excess physical activity 1104, because of the dependence of impedance on thorax blood flow. Furthermore, physiologic resting state measurements may be classified by posture at the time of measurement such that impedance attributes may be trended consistently according to position across time as the longterm ambulatory monitoring is highly susceptible to dynamic sensing environment noise that may reduce monitoring performance.

As with other biological readings, impedance readings are subject to biological variation between individuals and may take the form of different frequency ranges maximally affected by pathology. While general impedance measures are often taken between 1-100 KHz, individual differences may be learned as in FIG. 4 with an online or batch learning algorithm for personalization of impedance reading to reduce power and memory consumption by avoiding wide frequency range impedance sweeps. Maximally sensitive frequency ranges may be learned empirically in an initialization period 404, from a caregiver report 408, or from smartphone questionnaires 406, as an individual may self-report edema to validate impedance changes in their learned maximally sensitive frequency range. Narrowed frequency ranges personalized to the individual may conserve power to allow for more frequent sweeps or increased battery life without sacrificing monitoring performance.

In addition to being corrected by postural or activity data, impedance measures may be corrected for other patient characteristics that may alter the electrical impedance of biological tissue. As an example, it is known that adipose tissue has lower water content than other lean body tissue, and this may be used to correct for impedance measures where change in impedance in one body habitus may or may not be as severe as the same amount for another body habitus. An impedance attribute may thus include a correction in the form of a ratio with BMI, height, or weight such as from an electronic medical record 430.

As described earlier, remote monitoring is challenged by dynamic environments that may generate significant noise, FIG. 2. Examples of noise sources 240 affecting impedance include wet or dry sweat, mechanical separation of electrodes, hardware malfunction, or degraded electrode conductive gel. These complications may also affect sensing of other physiological quantities, such as EKG. These noise sources may be addressed by using the smartphone as an interrogative or reminding mechanism 222. For example, if sudden impedance changes are discordant with other sensors 212 or empiric trends, there may be excess sweat or electrolyte buildup on the skin that is altering the electrical path of injected current, and the resulting measure should not be used in the monitoring model. To determine if a common noise source is responsible for these findings, questionnaires or alerts 222 may be automatically sent to the smartphone 228 to ask the individual if there is a condition, such as excess sweat, poor electrode contact with skin, or electrode pads that have not been replaced on time. Furthermore, positional information from the accelerometer on device 226 displayed on the smartphone 228 may be used to guide the patient on placement of the adherent patch on the torso for optimal sensing and minimized chance of noise corruption, such as from separation or insufficient electrode distance. Furthermore, such information may help better characterize the patient. For example, an individual who does not replace electrode pads on schedule may suggest the patient is not fully compliant, and further modeling may use this information 138 to guide monitoring, classification, or alerting. For example, a non-compliant patient may not replace electrodes on time and risk poor electrical conduction with the skin, potentially manifesting as an aberrant hearth rhythm sensed by the EKG. Designation of the patient as poorly compliant may be used as a weight in the respective EKG derived attribute to modify the course of subsequent events and alerts as compared to a fully compliant patient.

Respiration

Respiratory function is an important parameter in monitoring health and disease, especially for pathologies with cardiopulmonary consequences such as heart failure or sleep apnea. As described above, the present invention avoids the excess sensor size and bulk of traditional respiratory sensors by specializing data acquisition with disseminated processing to extract information from smaller sensors with techniques described previously, FIG. 9. Time frequency decomposition techniques may be combined with cross-sensor fusion to produce attributes 414 and features from a chest-worn accelerometer on the sensing device for health monitoring and classification 418. For example, the EKG sensor may be used to align or validate respiratory signals from the accelerometer to enhance performance with methods such as weighting, averaging, cross-validation, stacking schemes, or other combinatory algorithms to extract respiratory rate and tidal volume.

A preferred embodiment uses the continuous phase consistency of changes in heart rate with chest excursion to validate the respiratory rate signal obtained from the accelerometer. A strong coherence between the phases of HRV and measured respiratory rate, as understood by the phenomenon of RSA, validates the respiratory and EKG findings and is advantageous in the setting of high noise environments. The phase coherence may be measured after time-frequency decomposition by comparing the phase, or complex part of the decomposed signal, of the same frequency between two signals or across different frequencies of the two signals. To assess cross frequency effects, phase of one frequency in one signal may be compared to changes in amplitude of the second signal to reveal an amplitude modulation, such as by using the envelope.

This method serves in contrast to existing phase comparison and coordination methods of electrical heart activity and respiration that purposely exclude large amounts of data from a signal, such as the EKG, and restrict phase comparison to select features, such as the R-spike. The presented invention enables a continuous phase comparison that may detect finer patterns in coherence and be used to better assess RSA for mutual validation of respiratory rate and hence reduce the need for more complicated respiratory sensing devices, such as respiratory inductive plethysmography.

Similarly, the presence or absence of RSA may suggest dysregulation of autonomic control as is known to occur with increased sympathetic tone in the context of chronic pathologies, such as heart failure. By characterizing the phase coherence between HRV and respiratory rate over time, changes in autonomic control may be monitored and constructed as attributes, such as by characterizing raw or normalized values in windows 1014, such as percentage change or z-scores.

To evaluate spectral activity in the context of respiratory phenomena, continuous or substantially continuous recording and storage of the accelerometer signal is used to accurately resolve the low frequency accelerometer components known to be influenced by respiration.

Certain aspects and patterns of respiration are also known to be correlated to disease outcomes and increased mortality as seen in pathologies such as heart failure and sleep apnea. Breathing patterns can be deduced by identifying and isolating the respiratory component of the accelerometer signal and using its envelope to characterize respiratory amplitude over time, giving an indication of tidal volume. The respiratory signal can be used to identify the presence, absence, or magnitude of breathing patterns such as Cheyne-Stokes or periodic breathing, where ventilation oscillates between hyperpnea and hypopnea or apnea, as seen in periodic breathing and Cheyne-Stokes, respectively. Time frequency decompositions, including wavelet transforms, Hilbert transforms, Fast Fourier Transforms, or other decomposition techniques may be used to find a spectral component correlated to the period of normal respiratory rate, of a breathing pattern, or of a pattern's envelope, and to identify any dynamic changes that may occur, possibly suggestive of a pathologic process. As an example, a ratio may be taken of peak-to-peak respiratory amplitudes occurring during a potential hypopneic or apneic event and an ordinary breathing interval. A measure of central tendency and dispersion may then be used to identify a pattern outside the individual's normal biological variation. Autocorrelation may also be used to find correlations between the respiratory signal and time lagged values of itself for conversion to the frequency domain to identify a spectral peak, and various thresholds may be applied to such techniques to validate the presence of a periodic signal or breathing pattern. Similarly, an apnea index may be constructed using averaged data across time of such events. These characterizations may then be used as attributes in the monitoring, classification, and prediction of health and disease.

A preferred embodiment uses an online learning algorithm to provide corrective factors for biological variation in detection of aberrant respiratory patterns or functions, such as periodic breathing, dyspnea, or tachypnea, to improve detection accuracy with personalized thresholds, FIG. 4. Personalization may be further accomplished by using other characteristics of patient history or empiric past data, FIG. 12 1206, such as averages, maximum, minimum, or other characteristics described previously. For example, normalization by measures of central tendency and dispersion account for a patient's empirical trends and avoid simpler, yet poorly consistent, absolute valued boundaries. Data inputs may be collected and validated through a variety of methods, including an initialization period 404, follow up patient visits 408, caregiver inputs, or smartphone questionnaire data 406, such as inquiring about quality of sleep in the context of apnea. These breathing patterns may be characterized by presence, absence, duration, magnitude, or other measures and used as attributes 416 for health monitoring or classification 418.

Another embodiment may include trends in respiratory rate and tidal volume as separate or combined values as attributes for the presented monitoring and classification system. An example of such an attribute is minute ventilation, a commonly used clinical surrogate of pulmonary function, calculated as volume of air respired per minute. The trend in such pulmonary function values may be characterized in a variety of ways, including but not limited to, measures of central tendency or dispersion in absolute or normalized units, rate of change, area under the curve, maximum and minimum values, and changes in response to activity level.

Such an embodiment may allow for distinction of apneic events caused by obstruction or nervous system control by using the accelerometer data to evaluate chest wall movement and simultaneous posture.

Static, dynamic, or both types of windows may be applied for a variety of purposes to accelerometer data, such as to determine characteristic values 1014, including measures of central tendency or dispersion, averages, medians, or modes, and to isolate intervals of data with minimal noise corruption 1006, such as excess movement, eating, coughing, or presence of position impeding data acquisition.

EKG

In the preferred embodiment, EKG detection is continuous or substantially continuous to provide indication of both acute changes in heart electrical activity, which may require immediate intervention 208, and chronic changes that have electrical manifestations, such as can be observed in heart failure. The layout of electrodes may be variable across the human body, reaching small electrode separation lengths to minimize discomfort to the long term continually monitored individual. The electrodes may also be shared with the impedance circuitry to further minimize space and weight requirements by the adherent patch. Distances may be adjusted, such as by an issued smartphone alert 222, if the sensed signal is poor in scenarios including, but not limited to, incorrect patch placement, poor mechanical contact, insufficient electrode distance, or degraded conductive adhesive.

Many EKG changes are known to be clinically relevant to monitoring health status, especially in the context of pathologies such as heart failure. Examples of such abnormalities include pattern and length of QRS complex, QT variability, T-wave alternans, HRV, and HRT. Some of these abnormal rhythms arise from the loss of proper autonomic balance stemming from weakened myocardium.

In a preferred embodiment FIG. 1, EKG analysis and processing is performed at multiple stages. At the sensing device level 100, basic rhythms are classified, comprising of bradycardia, tachycardia, pauses and blocks, and irregular rhythms. When wirelessly transferred to the smartphone 110, data may be compressed using a lossless algorithm such as Run Length Encoding, Huffman coding, or Lempel-Ziv-Welch. The compression may reduce the load on the cellular network, allow for transmission with commercial cellular plans for simplified patient usage, and enable faster information transfer of the encrypted data 134. At the remote server 112, more specific rhythms and patterns may be evaluated for, including atrial or ventricular tachycardia, bradycardia, or fibrillation, atrial flutter, premature ventricular contraction, TWA, and other irregular patterns involving elements of the EKG, such as QRS morphology or ST or QT segments.

Some abnormalities, such as HRV and HRT, are believed to result from increased sympathetic control or decreased vagal activity attempting to compensate for the weakened pumping function of the heart. Other changes, including TWA and QT interval, are believed to result at least in part from altered sensitivity of the myocardium to sympathetic control. Such attributes of the EKG may be derived using windowing FIG. 10 1014 with or without envelopes and characterized with further attributes, such as duration, frequency of rhythm per time interval, area under the curve, magnitude of irregularity, slope characteristic, or ratio of arrhythmia marker, such as slope, to characteristic of other physiological markers, such as age or mechanical heart, lung, or autonomic function that may be produced from the individual's electronic medical record 1016.

Some of these rhythm patterns that may be predictive of an emergent condition are preferentially apparent with varying heart rate. The disseminated processing model of the preferred embodiment of the adherent sensing patch allows for an individual's full engagement in daily activities and, as made possible by continuous or substantially continuous EKG recording, allows for sensing of such rhythms that are exposed by daily activity that would not be apparent to devices prohibiting daily activity. Furthermore, fusion methods described earlier, FIG. 9, may be performed on temporal windows, FIG. 10, maximally exposing such attributes. Examples of such attributes include ratios of heart rate and TWA duration or heart rate and QT duration, in time intervals of dynamic heart rhythm or rate.

Certain EKG patterns exhibit hysteresis, such as with dependence on current and past heart rate, and are hence maximally apparent in certain history-dependent states, though often subject to biologic variability. As monitoring progresses in the initialization period 404 and beyond, for 6 to 12 months, for example, monitoring data may be used to learn the states that are most susceptible to exhibiting these EKG patterns to optimally derive an attribute construction module 410 for characterizing and predicting health or disease state 418.

Some rhythms are known to have a dependence on lung function, such as the dependence of HRV on RSA. The presence of RSA is believed to be, in part, due to normal autonomic control that is disrupted in the excess sympathetic tone found in pathologies such as heart failure. Because of this dependence, preferred embodiments may increase accuracy of the HRV estimation attribute by weighting HRV values based on accelerometer derived respiratory activity, which may contaminate the true HRV manifestation, to favor HRV estimation during stable respiration.

Some rhythms are known to be implicated in sudden cardiac death, such as the length of the QT interval. Some medications and pathologies, such as heart failure, are also known to alter QT segment length. These changes may be monitored using the smartphone's medication log 426 in combination with the health and disease model to guide medication choice by physicians 126, especially in susceptible individuals, and for use as an attribute in classification.

EKG as Validator

The EKG signal provides insight into the timing of heart events and can be used to mutually validate other cardiac findings, such as by temporally restricting their detection. An example of such validation is the use of the EKG signal to align chest-worn accelerometer data in time to extract information on cardiac contraction and motion. Conversely, a physical activity attribute derived from the accelerometer data may be used to identify and filter physical activity data from the EKG signal, such as ectopic R waves.

A further example includes RSA as a phenomenon known to be influenced by respiration rate. RSA and HRV derived respiratory rate may be computed by a variety of techniques from the EKG signal and evaluated against other independent measures of respiratory rate. These different methods may be combined, such as with cross-validation, voting, weighting, or stacked generalization, to produce a respiratory rate attribute to input to the monitoring and classification system.

A further example includes sympathetic activation in pathologies such as heart failure. Physiological responses to decreased tissue perfusion include compensatory sympathetic stimulation, such as tachycardia and increased renin release from the kidneys leading to fluid retention. HRV may be filtered into low and high frequency components to reveal an underlying dysfunction in sympathetic tone or autonomic balance and be used to validate such other autonomic manifestations by methods described previously.

The EKG may also be used with the accelerometer to reveal reasons for aberrant movement, such as falls resulting from arrhythmias. Likewise, information from the accelerometer may inform the severity of an arrhythmia as physical movements, such as fainting or falling, may indicate a worse condition than asymptomatic arrhythmias detected solely by the EKG. The accelerometer may also be used as a cross sensor validation in the event that contact electrodes have reduced or impaired contact with the body, as may occur in vigorous body movement, perhaps due to the environment, that should not be confused with a true arrhythmia.

General Patient Data

Various attributes of patient data may be collected from the individual, such as at initialization point 404 or from electronic medical record 430, for improved accuracy of health or disease state classification or prediction. Patient data may be constructed into attributes to effectively personalize modeling, classification, and prediction to the individual. As such, patients are inherently evaluated according to their personal risk factors across multiple domains.

As an example, demographic data may be used as one or multiple attributes and may include age, race or ethnicity, genetic information or predispositions, occupation, education level, socioeconomic level, or geographic location.

As a further example, past medical history may be used as one or multiple attributes and may include kidney function, diabetic status, hypertension, coronary artery disease, respiratory disease, arrhythmias, body mass index, dementia, NYHA heart failure class, or compliance.

These patient characteristics may be discrete measures transformed to scales or may be characterized to arbitrary units. For example, a binary valued presence/absence of diabetes mellitus parameter may be characterized by a categorical diabetes burden attribute that takes into account the number of years since diagnosis, most recent HgbA1C level, average blood sugar without medication, presence of nephropathy, neuropathy, or retinopathy, or other characterizations.

The above individual or combined values may be further combined through various mathematical operations, such as linear combinations or ratios, in attribute construction 410.

Other data points may be added to the monitoring system that enhance performance but are not directly detected by the sensing device. Such attributes may be input to the remote server 432, such as through a web form or automated script using an API. Examples of such attributes include blood pressure, SpO2, ejection fraction, blood chemistries, including BUN, ck-mb, troponin, or BNP, weight, history of IHD, or clinical impression.

Initialization and Training

As in FIG. 4, to correlate sensor readings to physiological changes, the detection method must undergo a period of supervised sensing 404 to correlate true system changes to changes in sensor readings. The sensing device outputs may be correlated to a traditional clinical measure 428, such as a gold standard, by any number of methods, including a supervised learning method such as a regression technique that minimizes error between signals, or an unsupervised technique to find correlative patterns in data that may not be readily apparent otherwise. Error patterns may be identified and minimized in a supervised or unsupervised model by using raw, derived, filtered, or otherwise processed signals. Error signals may also be evaluated for different locations or positions of sensor placement. Such correlations may or may not be linear depending on the dependencies of the sensing device and the gold standard measurements.

Examples of physiological system changes whose sensing device measurements may be validated include, by way of example, changes in fluid retention, organ function, respiratory, hemodynamic, or temperature homeostasis, position and posture, as well as environmental influences. The various state-dependent biases introduced by the recording mechanism can be understood in this way and corrected for to improve classification and monitoring performance. The corrections may be applied to raw, fused, or otherwise processed values and may thus be a component in their construction as attributes.

An example of a validation measure includes an external temperature signal, such as 412, that may be combined with a measure of activity level, such as in 410 by a mathematical function. This combined value may then be compared to a clinical measurement of temperature 428. As a further example, impedance reading may be combined with a temperature reading in a similar fashion to correct for cutaneous vasodilatory effects for comparison to accepted clinical measurement.

A supervised initialization period 404 may also be implemented when the device is applied to a new individual to enable algorithmic learning of the sensed individual's biological variation to allow personalized monitoring, classification, and prediction of health or disease state. The initialization period may be of variable duration and depend on length of patient stay in the hospital, which is a convenient setting for initialization and training because of the presence of physicians to offer clinical impressions on patient state 408. Such a period may occur after hospitalization for an emergent condition, such as decompensated heart failure, which may have a hospital stay and hence initialization period of several days or weeks.

The general algorithm for health and disease monitoring, classification, and prediction must also be trained with representative data collected from a broad population over many time points. The needed population size may vary depending on the number of features or dimensions used to construct the model, and may be a number ranging from 100 to 1000. The population must also provide a valid distribution across attribute states to adequately train the learning model.

After training, the proposed model may then be subject to various cross-validation test methods or stacked generalization after training to evaluate 136 and improve modeling accuracy. Such validation methods may evaluate multiple models 134 based on one or several sets or feature combinations and test performance on a wholly or partly different set of training data, such as with k-fold cross validation.

Data Transmission

The presented method meets the need for improved longterm health and disease monitoring and emergent condition prediction in part due to a disseminated processing system to minimize the computation and transmission load in locations sensitive to power and memory demand and form factor size. In the preferred embodiment, the adherent patch 100 variably processes 134 sensed data and transmits results wirelessly 136 to a smartphone intermediate device 110 for further processing, and a transmission of encrypted data 134 is made to a remote server 112 for further computation and hosting 152 to the healthcare team and caregivers 122. Such dissemination allows for decreased sensing device size and hardware requirements, as well as decreased bandwidth requirements to facilitate integration with existing public cellular infrastructure.

Data on the device may be processed in realtime for acute conditions necessitating immediate intervention, such as the presence of fatal arrhythmias in the EKG signal comprising tachycardia, bradycardia, pauses or blocks, or irregular rhythm. Delayed processing is favored for data not used for monitoring acute conditions and is cached and eventually loaded to non-volatile memory 242, such as EEPROM or flash memory. Non-volatile memory may store and continually add sensed data until triggered 246 or 204 to transmit data to intermediate device to minimize transmission overhead waste. Triggers may be a programmed schedule 246 or override, such as from emergent alert 208 or depleted memory capacity 230, that transmits 248 data stored in non-volatile memory via wireless protocol, such as Bluetooth or Wi-Fi, to the smartphone intermediate device. The programmed schedule may be adjusted 216 for increased transmission frequency to allow for realtime diagnosis if desired by a caregiver. In the event of disrupted communication between sensing and intermediate device, the non-volatile memory storage has sufficient capacity to store patient data for an extended period of time, such as days, weeks, or months, to provide clinical continuity.

Data transmission and storage may be monitored for integrity by using any number of error detection systems, including check sum or cyclic redundancy check.

Smartphone

The intermediate device 110, such as a smartphone, may contain a processor for tasks such as compression or further data analysis prior to transmission 154, via wireless protocol including, but in no way limited to, 3G, 4G, LTE, or Wi-Fi, for further processing or hosting of data by remote server 112.

Remote Server

The remote server receiving data from the intermediate device may contain a processor for decompression and further processing without the limitations of space and power present in previous system stages. Learning algorithms from historical empiric data may be run on the processor, along with any other processing steps to construct attributes or transform them to features for health monitoring, classification, or prediction.

A number of learning methods may be employed that are either supervised or unsupervised in nature, depending on the collected data and initialization technique, to improve the classification algorithm. These may be enforced by continual updating from longterm data collection from sensing devices and outcomes data provided by caregivers and the healthcare team 408.

A number of classification techniques may be used, such as regression, support vector machines, or neural networks, to utilize features in classifying health state and predicting emergent conditions at any stage in the present method, such as the remote server 112.

The remote server 112 may also be a host for sensed data and processing, such as composite scores, historical trends, or predictions. Data may be accessed through an authenticated system 152 complying with health information regulations and may be accessible via the internet through a variety of portals, including browser, smartphone, software or method utilizing an API, phone lines, or cellular or satellite connections. The data may be accessible with varying permission levels that may be set for caregivers, family members, friends, the monitored individual, or researchers 128. Software on the remote server may include a mixture of computational routines and web hosting 152 or visualization routines 120 in various programming languages.

In the preferred embodiment, data transmission may be bidirectional to send data or commands from device 100 or 110 to remote server 112 and to send programming updates or commands from remote server 112 to device 100 or 110. As an example, sensing and transmission intervals may be controlled by a healthcare provider from the remote server.

Many variations of this disseminated processing scheme are realizable, such as variably processed signal sets, such as raw, averaged, derived, or filtered, at any system stage and do not depart from the presented method.

Data Security

PHI stored or transmitted at any stage must be encrypted according to medical regulation. The presented method may use a variety of techniques to minimize the amount of PHI that is collected and transmitted such as to minimize any security risks and unnecessary encryption and decryption computation. In a preferred embodiment, all PHI including any number of patient characteristics, such as date of birth, name, past medical history, or phone numbers, may be collected at the time of device and algorithm initialization and encrypted on the remote server 112. Such information may be collected by a variety of methods, such as a web form. At such a time, a non-reverse-identifiable code may be automatically issued to the patient's sensing device 100 by the remote server 112 or vice versa. Subsequent activity may then be limited to collection of non-PHI data from sensing device and smartphone using the non-reverse-identifiable code to link sensed data to patient profile at the encrypted remote server, as detailed in patent application US20090076346 that is hereby incorporated by reference in its entirety.

If regulation deems data is PHI or sensing requirements require PHI data usage, encryption schemes defined by regulatory agencies and known in the art may be implemented at all stages in the data acquisition and processing system.

Data may also be separated in sets containing PHI from sets not containing PHI. In such an implementation, only selective data sets would require encryption throughout the system, such as at storage or transmission, at stages including sensing device, smartphone, or remote server.

Alerting

As in FIG. 2, the classification algorithm can issue customizable alerts depending on the sensed individual's health status. Alerts can be issued when an individual is classified as being in danger of an emergent condition 208, such as having entered decompensated heart failure. Alerts may also be issued when a composite index of health reaches a user defined threshold 210. For example, a heart failure index may be programmed to alert a healthcare provider when there is a particular probability of decompensation. Such composite scores can be elected to be transmitted to healthcare personnel 202 at specific time intervals, as well. Issued alerts may take many forms, including but not limited to, SMS, phone call, web-based or smartphone application alert, email, or faxable report. Alerts may be issued at the remote sensing stage, including sensing 226 and intermediate 228 device, such as questionnaire, battery change alert, electrode contact alert, or conductive gel replacement alert, by SMS, phone call, email, faxable alert, smartphone or web-based application alert, device vibration, device audio alert, or device visual alert. Alerts may also be issued to emergency medical services, concierge medical services, or family members 232 through similar mechanisms described above.

A healthcare professional alerted to a certain emergent condition, such as ADHF, may instruct the patient to adjust a drug dosage 218, such as that of a diuretic, beta-blocker, or inotrope. Independently or in combination, a clinic visit may be scheduled with desired priority level.

One form of alert may be on the interface linked to the remote server hosting patient data and health status 152 to be accessed by the healthcare provider 122. Alerts on such healthcare resource visualizations 120 may be in many forms, such as static or dynamic changes in color, font or line weight, or priority in a queue, to alert any member of the healthcare team, such as a nurse of physician, to intervention.

Due to the importance of clinical judgment in assessing and predicting health status, a healthcare provider 202 may wish to increase the sensitivity of detection based on their impression of the individual 216. This can be accomplished by a variety of methods, such as by changing the frequency or mode of alert issuance, by constructing a classification attribute related to clinical impression, or by associating the desired alerting technique with the physician's profile.

As described earlier, some embodiments may modify sensing or processing parameters of the sensing device or collected data in response to alert states 216. As an example, discordant sensor readings 212 may trigger increased sampling of certain sensors to evaluate the source of discordance, such as mechanical or electrical error or true patient physiological reading. Such alerts may be verified by smartphone questionnaire 222 sent to the individual inquiring about the self-reported state of health or state of device attachment.

Also as described earlier, alerts may be combined with therapeutic delivery 218, such as drug elution with inotropic or antiarrhythmic agents, temperature maintenance, pacing, defibrillation, or pump assist activity. Such therapies may be useful in ADHF or lethal arrhythmias.

Visualizations

Raw data collected from the sensing device may be poorly interpretable without appropriate processing or mapping. Data that is filtered or further transformed, such as through normalization, averaging, correction factors, or cross-sensor correlations, may be better related to traditional clinical measures and more easily interpreted. Furthermore, casting data as plots, such as against time or other quantities, may expedite interpretation of the large datasets over time, as in plotting composite scores longitudinally, FIG. 8.

Hosted data may be displayed through secure web pages requiring authentication to protect PHI. Trends, such as 804, may be more easily visualized with automated reference statistics 800 or 802 or normalized composite indices for quick interpretation of aggregated data. Different colors, weights, or line styles may be used to draw attention to areas of greater perceived importance in plots, such as threshold crossings or significant changes from historical data.

More information can be made available, such as past data, absolute values, or raw measurements, in pages after the main report page.

Sensing device or intermediate device data may also be viewed, such as device health, number of malfunctions, or battery status.

While numerous embodiments of the present invention have been shown and described herein, one of ordinary skill in the art will appreciate that such embodiments are provided by way of example only. Numerous variations, changes, and substitutions will now occur to those skilled in the art without departing from the invention. It should be understood that various alternatives to these embodiments of the invention described herein may be employed in practicing the invention. It is intended that the following claims define the scope of the invention and its methods and structures within the scope of these claims and their equivalents be covered thereby.

What is claimed is:

1. A wearable body sensor patch for monitoring a health state of a patient, comprising:
an accelerometer;
a first electrode pad disposed on the patch and configured to be adhesively attached to the skin of a patient;
a second electrode pad disposed on the patch and configured to be adhesively attached to the skin of the patient;
a microphone (i) integrated with the first pad, (ii) having a hole or a funnel bored in a non-conductive area of the first pad, (iii) configured to have a direct air or diaphragm contact with the patient's chest wall disposed on the patch, (iv) configured to detect cardiac and pulmonary acoustic signals continuously for six to twenty-four hours during which the patient performs a plurality of daily activities in an outpatient setting including walking, sitting and sleeping, and (v) configured to be coupled to one of a mobile cellular device or a remote server; and
the patch having a generally rectangular shape and rounded edges and a form factor approximately the size of a human palm; wherein,
the one of the cellular device or the remote server is configured to provide information related to the signals to a remote healthcare provider in one of a time delayed or a real time manner;
the accelerometer determines noise level and determines if the patient is walking, sitting or sleeping;
data associated with the microphone is read for the six to twenty-four hours in windows of static or dynamic duration lengths, wherein the reading windows are initiated based on the noise level and during each of the plurality of daily activities to monitor patient compliance;
the first pad provides acoustic insulation to the microphone and a snug contact between the microphone and the chest wall; and
the patch is reusable by the patient for at least one month.

2. The patch of claim 1, wherein the remote server or the cellular device instructs the wearable body sensor patch to one of stop processing or stop transmitting data generated by the microphone if the data generated by accelerometer indicates that the ambient noise is above a predetermined threshold level.

3. The patch of claim 1, wherein the remote server or the cellular device instructs the wearable body sensor patch to reduce a duty cycle associated with the operation of the microphone if the data generated by accelerometer indicates that the ambient noise is above a predetermined threshold level.

4. The patch of claim 1, wherein the microphone includes one of a direct air microphone without a diaphragm or a contact microphone including a diaphragm.

5. The patch of claim 1, wherein the remote server is configured to isolate data related to pulmonary acoustic signals from data related to cardiac acoustic signals.

6. The patch of claim 1, further comprising: the wearable body sensor patch includes an electrocardiogram sensor and wherein the remote server is configured to validate the information associated with the acoustic signals by comparing it with data associated with the electrocardiogram sensor.

7. The patch of claim 1, further comprising:
the microphone includes an intake portion, wherein the intake portion is elevated above the first and second electrodes.

8. The patch of claim 1, further comprising: the first electrode pad includes a first surface facing the patch and rigidly attached to the patch and a second surface facing away from the patch and configured to adhere to a patient's skin.

9. The patch of claim 1, further comprising: the second electrode pad includes a first surface facing the patch and rigidly attached to the patch and a second surface facing away from the patch and configured to adhere to a patient's skin.

10. The patch of claim 1, wherein the remote healthcare provider includes one of a physician, a nurse, a caregiver, a family member of the patient, or a friend of the patient, wherein the healthcare provider is remotely located from the patient.

11. The patch of claim 1, wherein the microphone is configured to detect cardiac and pulmonary acoustic signals to monitor the patient for heart failure or sleep apnea when the patient is sleeping in an outpatient setting.

12. The patch of claim 1, wherein the one of the cellular device or the remote server is configured to provide information related to the signals to a remote healthcare provider in a real time manner if the information indicates an acute condition.

13. The patch of claim 1, wherein the one of the cellular device or the remote server is configured to provide information related to the signals to a remote healthcare provider in a time delayed manner if the information relates to a condition that is not an acute condition.

* * * * *